(12) United States Patent
Peyrelevade

(10) Patent No.: US 7,437,344 B2
(45) Date of Patent: Oct. 14, 2008

(54) USE OF ARTIFICIAL INTELLIGENCE IN PROVIDING BEAUTY ADVICE

(75) Inventor: Jerome Peyrelevade, Paris (FR)

(73) Assignee: L'Oreal S.A., Paris (FR)

( * ) Notice: Subject to any disclaimer, the term of this patent is extended or adjusted under 35 U.S.C. 154(b) by 1127 days.

(21) Appl. No.: 10/024,616

(22) Filed: Dec. 21, 2001

(65) Prior Publication Data

US 2003/0065636 A1    Apr. 3, 2003

Related U.S. Application Data

(60) Provisional application No. 60/325,559, filed on Oct. 1, 2001.

(51) Int. Cl.
| | |
|---|---|
| G06F 15/00 | (2006.01) |
| G06F 15/18 | (2006.01) |
| G06F 17/30 | (2006.01) |
| G06F 7/00 | (2006.01) |
| G06Q 30/00 | (2006.01) |

(52) U.S. Cl. .............................. 706/62; 705/26; 705/27
(58) Field of Classification Search .................... 706/48, 706/20, 62; 434/377, 262; 382/100, 162, 382/276, 118; 345/646; 705/23, 14, 37, 705/26–28, 10; 709/218, 239; 707/3; 281/15.1, 281/37, 38, 43; 132/100; 355/79

See application file for complete search history.

(56) References Cited

U.S. PATENT DOCUMENTS

| | | | | |
|---|---|---|---|---|
| 4,232,334 A | * | 11/1980 | Dyson | .......................... 348/77 |
| 4,842,523 A | * | 6/1989 | Bourdier et al. | ............. 434/371 |
| 5,751,829 A | | 5/1998 | Ringland et al. | |
| 6,091,836 A | | 7/2000 | Takano et al. | |
| 6,260,024 B1 | | 7/2001 | Shkedy | |
| 6,293,284 B1 | | 9/2001 | Rigg | |
| 6,707,929 B2 | * | 3/2004 | Marapane et al. | ........... 382/100 |
| 6,719,565 B1 | * | 4/2004 | Saita et al. | ..................... 434/94 |
| 6,761,697 B2 | * | 7/2004 | Rubinstenn et al. | ......... 600/587 |
| 7,324,668 B2 | * | 1/2008 | Rubinstenn et al. | ......... 382/118 |
| 2001/0011818 A1 | | 8/2001 | Dockery et al. | |
| 2001/0014868 A1 | | 8/2001 | Herz et al. | |
| 2002/0019763 A1 | * | 2/2002 | Linden et al. | ................. 705/10 |
| 2002/0024528 A1 | * | 2/2002 | Lambertsen | ................ 345/646 |

(Continued)

FOREIGN PATENT DOCUMENTS

EP        0 226 959        7/1987

(Continued)

OTHER PUBLICATIONS

Aarabi et al; The automatic measurement of facial beauty; IEEE International Conference on Systems, Man, and Cybernetics; vol. 4; Oct. 7-10, 2001; pp. 2644-2647.*

(Continued)

*Primary Examiner*—Michael B Holmes
(74) *Attorney, Agent, or Firm*—Finnegan, Henderson, Farabow, Garrett & Dunner, L.L.P.

(57) ABSTRACT

The invention may involve using an artificial intelligence engine to provide beauty advice. Beauty advice may include a recommendation for a product. The recommended product may be complementary to a second product. The second product may be a user-selected product. A notification of the recommended product may be provided to the user.

89 Claims, 26 Drawing Sheets

U.S. PATENT DOCUMENTS

| | | | | |
|---|---|---|---|---|
| 2002/0035611 | A1* | 3/2002 | Dooley | 709/218 |
| 2002/0054714 | A1 | 5/2002 | Hawkins et al. | |
| 2003/0061202 | A1* | 3/2003 | Coleman | 707/3 |

FOREIGN PATENT DOCUMENTS

| | | | |
|---|---|---|---|
| EP | | 226959 A2 * | 7/1987 |
| EP | 1 030 267 | | 8/2000 |
| EP | 1 134 701 | | 9/2001 |
| EP | 1 169 964 | | 1/2002 |
| WO | WO 98/20458 | | 5/1998 |
| WO | WO 99/23609 | | 5/1999 |
| WO | WO 00/33271 | | 6/2000 |
| WO | WO 00/76398 | | 12/2000 |
| WO | WO 01/04838 | | 1/2001 |
| WO | WO 01/04840 | | 1/2001 |
| WO | WO 01/18674 | | 3/2001 |
| WO | WO 01/20517 | | 3/2001 |
| WO | WO 01/57771 | | 8/2001 |
| WO | WO 01/77976 | | 10/2001 |
| WO | WO 01/80122 | | 10/2001 |
| WO | WO 01/87245 | | 11/2001 |
| WO | WO0187245 A2 * | | 11/2001 |
| WO | WO 01/91600 | | 12/2001 |
| WO | WO 01/91601 | | 12/2001 |
| WO | WO 02/03232 | | 1/2002 |
| WO | WO 02/05249 | | 1/2002 |
| WO | WO0205249 A2 * | | 1/2002 |
| WO | WO 02/37421 | | 5/2002 |
| WO | WO 02/082350 | | 10/2002 |

OTHER PUBLICATIONS

Zhang et al; Scenic beauty estimation using independent component analysis and support vector machines; IEEE Southeastcon Proceedings; Mar. 25-28, 1999; pp. 274-277.*

Katsenelinboigen; Beauty as a measurement of performance: an introduction to the calculus of predispositions; 5th IEEE International Symposium on Intelligent Control Proceedings; Sep. 5-7, 1990; pp. 98-103; vol. 1.*

Ngo et al; Aesthetic measure for screen design; Proceedings Computer Human Interaction Conference; Nov. 30- Dec. 4, 1998; pp. 64-71.*

Yin Wu, et al., "A Plastic-Visco-Elastic Model for Wrinkles in Facial Animation and Skin Aging", MIRALab, 1998.

Catherine Pelachuad, et al., "Final Report to NSF of the Standards for Facial Animation Workshop", The Institute For Research In Cognitive Science, University of Pennsylvania, IRCS Report 94-21, Nov. 1994, pp. 1-62.

Co-pending U.S. Appl. No. 10/024,480, Body Image Enhancement, Gilles Rubinsteen et al., filed Dec. 21, 2001, Preliminary Amendment filed Apr. 22, 2002.

Co-pending U.S. Appl. No. 10/024,354, Methods and Systems for Predicting And/Or Tracking Changes in External Body Conditions, Gilles Rubinstenn et al., filed Dec. 21, 2001, Preliminary Amendment filed Apr. 22, 2002.

Co-pending U.S. Appl. No. 10/024,333, Methods and Systems for Generating A Prognosis, Gilles Rubinstenn et al., filed Dec. 21, 2001, Preliminary Amendment filed Apr. 22, 2002.

Co-pending U.S. Appl. No. 10/024,622, Historical Beauty Record, Daniela Giacchetti et al., filed Dec. 21, 2001, Preliminary Amendment filed Apr. 22, 2002.

Co-pending U.S. Appl. No. 10/024,332, Identification and Presentation of Analogous Beauty Case Histories, Gilles Rubinstenn, filed Dec. 21, 2001, Preliminary Amendment filed Apr. 22, 2002.

Co-pending U.S. Appl. No. 10/024,481, Interactive Beauty Analysis, Gilles Rubinstenn et al., filed Dec. 21, 2001, Preliminary Amendment filed Apr. 22, 2002.

Co-pending U.S. Appl. No. 10/024,495, Feature Extraction in Beauty Analysis, Gilles Rubinstenn et al., filed Dec. 21, 2001, Preliminary Amendment filed Apr. 22, 2002.

Co-pending U.S. Appl. No. 10/024,353, Simulation of an Aesthetic Feature on a Facial Image, Daniela Giacchetti et al., filed Dec. 21, 2001, Preliminary Amendment filed Apr. 22, 2002.

Co-pending U.S. Appl. No. 10/024,496, Beauty Advisory System and Method, Gilles Rubinstenn et al., filed Dec. 21, 2001, Preliminary Amendment filed Apr. 22, 2002.

Co-pending U.S. Appl. No. 10/024,620, Virtual Beauty Consultant, Daniela Giacchetti et al., filed Dec. 21, 2001, Preliminary Amendment filed Apr. 22, 2002.

Co-pending U.S. Appl. No. 10/024,334, Calibrating Image Capturing, Gilles Rubinstenn, filed Dec. 21, 2001, Preliminary Amendment filed Apr. 22, 2002.

Co-pending U.S. Appl. No. 10/024,352, Shop-In-Shop Website Construction, Jerome Peyrelevade et al., filed Dec. 21, 2001.

Co-pending U.S. Appl. No. 10/024,619, Early Detection of Beauty Treatment Progress, Francis Pruche et al., filed Dec. 21, 2001, Preliminary Amendment filed Apr. 22, 2002.

Co-pending U.S. Appl. No. 10/024,356, Cosmetic Affinity Indexing, Daniela Giacchetti et al., filed Dec. 21, 2001.

Co-pending U.S. Appl. No. 10/024,621, Systems and Methods for Providing Beauty Guidance, Daniela Giacchetti et al., filed Dec. 21, 2001, Preliminary Amendment filed Apr. 22, 2002.

Co-pending U.S. Appl. No. 10/024,355, Methods and Systems Involving Simulated Application of Beauty Product, Jerome Peyrelevade et al., filed Dec. 21, 2001, Preliminary Amendment filed Apr. 22, 2002.

Co-pending U.S. Appl. No. 10/024,351, Customized Beauty Tracking Kit, Gilles Rubinstenn et al., filed Dec. 21, 2001, Preliminary Amendment filed Apr. 22, 2002.

Co-pending U.S. Appl. No. 10/024,615, Analysis Using a Three-Dimensional Facial Image, Gilles Rubinstenn et al., filed Dec. 21, 2001, Preliminary Amendment filed Apr. 22, 2002.

Co-pending U.S. Appl. No. 10/024,482, Body Image Templates With Pre-Applied Beauty Products, Daniela Giacchetti, filed Dec. 21, 2001, Preliminary Amendment filed Apr. 22, 2002.

Co-pending U.S. Appl. No. 10/024,651, Image Capture Method, Gilles Rubinstenn, filed Dec. 21, 2001, Preliminary Amendment filed Apr. 22, 2002.

Co-pending U.S. Appl. No. 10/024,034, Devices and Methods for Enabling Evaluation of Typological Characteristics of External Body Portions, and Related Devices, Roland Bazin, filed Dec. 21, 2001.

English Abstract of KR 20010067927.

* cited by examiner

PERSONAL BEAUTY CONSULTANT

YOU HAVE SELECTED ABC'S RUBY RED LIPSTICK. BASED ON YOUR CONFIDENTIAL PERSONAL PROFILE, OUR COMPUTERIZED BEAUTY ASSISTANT HAS IDENTIFIED THE FOLLOWING COMPLEMENTARY PRODUCTS UNIQUELY CUSTOMIZED TO YOU!

 ABC CREAM CONCEALED   $28.44    [BUY NOW]   [LEARN MORE]

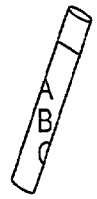 ABC FIRE LIPLINER   $18.23    [BUY NOW]   [LEARN MORE]

 ABC HYPER MASCARA   $14.94    [BUY NOW]   [LEARN MORE]

 ABC HOT EYES EYESHADOW   $16.62    [BUY NOW]   [LEARN MORE]

[BACK]

[HOME]

FIG. 2

PERSONAL CONSULTANT

YOUR SELECTION OF ABC'S RUBY RED LIPSTICK IS DISPLAYED BELOW. CLICK ON A PERSONOLIZED PRODUCT SELECTION TO SEE HOW RUBY RED LIPSTICK WILL LOOK WITH COMPLEMENTARY PRODUCTS!

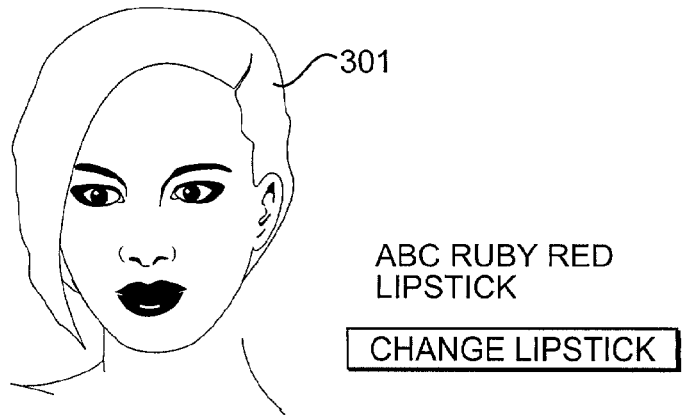

ABC RUBY RED LIPSTICK

CHANGE LIPSTICK

 ABC CREAM CONCEALER $28.44   APPLY TO IMAGE   BUY NOW   LEARN MORE

 ABC FIRE LIPLINER $18.23   APPLY TO IMAGE   BUY NOW   LEARN MORE

 ABC HYPER MASCARA $14.94   APPLY TO IMAGE   BUY NOW   LEARN MORE

 ABC HOT EYES EYESHADOW $16.62   APPLY TO IMAGE   BUY NOW   LEARN MORE

*FIG. 3*

PRODUCT INFORMATION — 710

PRODUCT A

TYPE (SKINCARE, MAKEUP, HAIRCARE,) ACCESSORIES, APPAREL, ...
    MAKEUP (LIPSTICK, FOUNDATION, EYE SHADOW, ...)
    COLOR (RED, RUST, BROWN, PURPLE, ...)
    COMPATIBLE SKIN TYPE (DRY, OILY, COMBINATION, ...)
    COMPATIBLE SKIN TONE (LIGHT, MEDIUM, DARK, ...)
    COMPATIBLE EYE COLOR (BLUE, GREEN, BROWN, ...)
    COMPATIBLE HAIR COLOR (BLOND, BROWN, BLACK, ...)
    •
    •
    •
    INTER-COSMETIC COMPATIBILITY (PRODUCT E,F,G, ...)
    NON-COSMETIC COMPATIBILITY (PRODUCT X,Y, Z,...)
•
•
•
PRODUCT Z

EXPERT ADVICE

PRODUCT RELATIONSHIP

TREATMENT FOR CONDITION

• • • COLOR COMPATIBILITY

*FIG. 15*

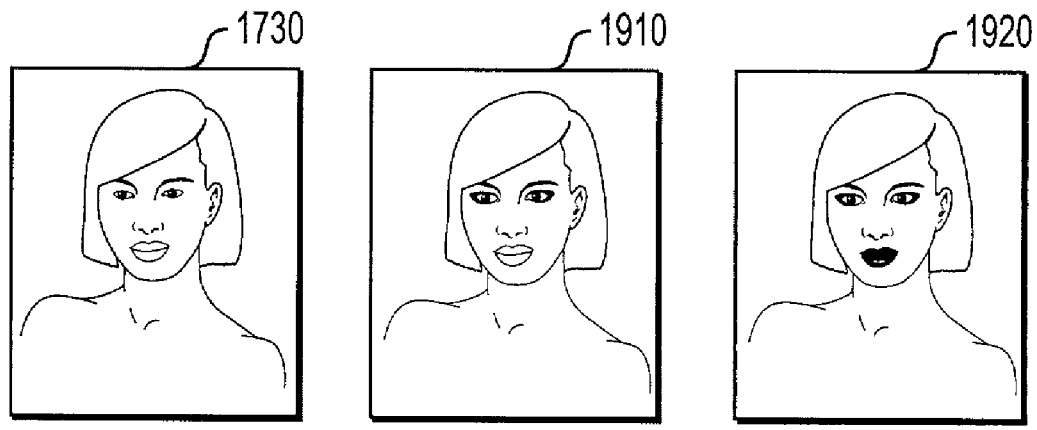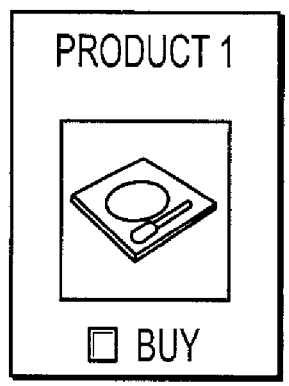
*FIG. 19*

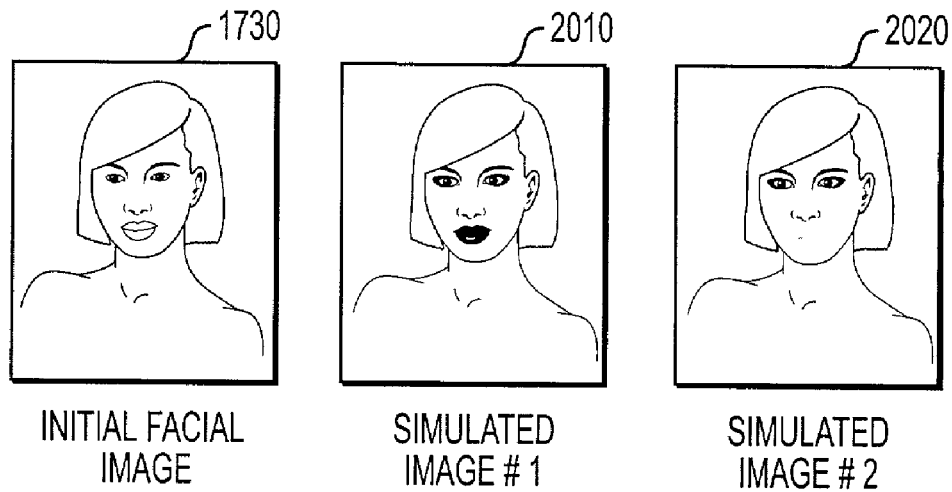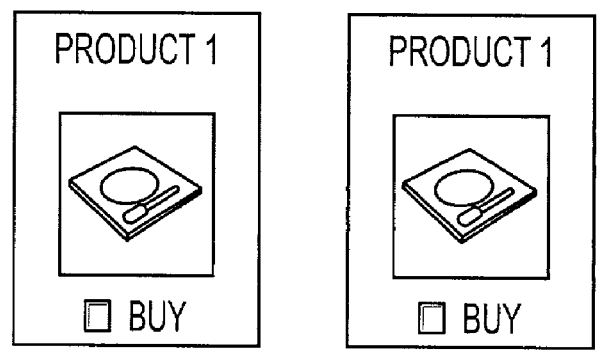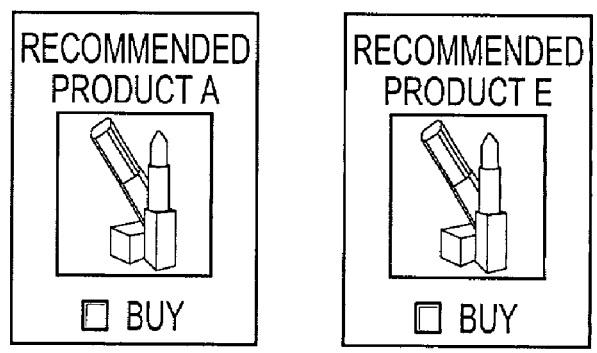
FIG. 20

USE OF ARTIFICIAL INTELLIGENCE IN PROVIDING BEAUTY ADVICE

This application claims priority to U.S. provisional application No. 60/325,559, filed Oct. 1, 2001.

BACKGROUND OF THE INVENTION

1. Field of the Invention

The invention relates to methods, combinations, apparatuses, systems, and articles of manufacture for making product recommendations. In one aspect, the invention may employ an artificial intelligence engine for providing beauty advice. In another aspect, the invention may relate to a simulation of selected beauty products or recommended beauty products on a image.

2. Description of Related Art

Although the invention, in its broadest sense, is not limited to any particular products, for purposes of explaining some inventive features and principles, the invention is described herein in connection with beauty products and accessories.

The selection of beauty products is often a function of personal characteristics of a wearer. These characteristics may include the wearer's lifestyle, color preferences, body chemistry, fashion preferences, and/or physical attributes. Thus, a lipstick shade that works well on a young, blond-haired, fair-skinned woman may not work well on a more mature, dark-haired, dark-skinned woman. Beauty professionals, be they located at beauty facilities, or retail establishments or other locations, are therefore often relied upon for assistance in beauty product selection. Of course, the ability to obtain helpful advice is both a function of a level of personal attention available and a skill level of the beauty professional offering the advice. For example, if a beauty counter in a retail establishment does not have sufficient staff to handle customer traffic or if the staff is improperly trained, the quality of advice may suffer.

In both brick and mortar and e-commerce environments, beauty product purchase decisions are often multi-tiered. That is, consumers may not only need help selecting a first product for purchase, but they often require assistance selecting one or more additional products that complement the first-selected product. For example, after a costumer selects a lipstick, she may desire lipliner and blush that complement the lipstick. The desire for complementary products may likely be a function not only of the chosen shade of the lipstick, but also of the lifestyle, preferences, and personal attributes of the wearer.

In many retail establishments, sales persons are specialized. Those who work in a beauty department may often have limited knowledge of products available in other departments. Thus, the ability of beauty sales persons to cross-sell clothing and accessory items is likely to be restricted. Yet, the information gained during the beauty product purchasing process could be very helpful in recommending clothing and accessory products well suited to the customer's lifestyle, and/or also complementary to recently acquired beauty products.

SUMMARY OF A FEW ASPECTS OF THE INVENTION

One aspect of the invention may employ an artificial intelligence engine to aid in determining and/or identifying beauty advice related to user-specific information. The user-specific information may include a user-selected product or any other information relating to the user. The beauty advice may include a recommended product. The recommended product may be any beauty product, such as a cosmetic product (e.g., makeup or care product or service) or non-cosmetic product (e.g., accessories or apparel). In one embodiment, the identification of a recommended product may also be based on product characteristics, user preferences, populational data, or expert advice. The recommended product may also be chosen based on either aesthetic, ethical, physical, physiological, and/or biological compatibility. The recommended product may be complementary to the user-selected product.

Another aspect of the invention may simulate an application of a selected beauty product and/or a recommended product on a body image. The simulation may be carried out in many ways, including simulating an application of a selected product and simulating an application of one or more of a complementary product and/or an additional recommended product. The simulation may occur in any order, for example, sequentially or simultaneously. Also, the simulation may be activated in any manner, including selecting from a plurality of button options or a toggle between simulated images. In one embodiment, the invention may simulate the application of beauty products on a facial image with differing combinations of products. In another embodiment, queries may be made to a user to determine acceptability of beauty products.

As described hereafter, other aspects of the invention exist, for example, in details of exemplary cosmetic and non-cosmetic product constructs, as well as in details of the recommended product selection and simulated application schemes. Thus, this summary of a few aspects of the invention is not to be interpreted as defining the invention in its broadest sense.

BRIEF DESCRIPTION OF THE DRAWINGS

FIG. 2 illustrates an exemplary list of recommended products consistent with the invention;

FIG. 3 illustrates an exemplary initial product selection displayed on an image consistent with the invention;

FIG. 8 is a table illustrating exemplary product information consistent with one aspect of the invention;

FIG. 15 is a table illustrating exemplary expert advice information consistent with an embodiment of the invention;

FIG. 19 is a first exemplary display of a visual simulation feature according to an embodiment of the invention;

FIG. 20 is a second exemplary display of a visual simulation feature according to an embodiment of the invention;

DESCRIPTION OF EXEMPLARY EMBODIMENTS

Reference will now be made in detail to the invention, examples of which are illustrated in the accompanying drawings. The same reference numbers may be used throughout the drawings to refer to same or like parts.

The invention may be used to aid consumers in obtaining beauty advice. That is, based on user-specific information, the invention may provide a consumer beauty advice, such as recommended products. The recommended products may complement (physically, ethically, physiologically, biologically, and/or aesthetically) a user-selected product(s). The recommendation of complementary products may not only be a function of prior product selection but may also be a function of personal characteristics of the consumer. So, for example, based on a selection of ABC company's Ruby Red lipstick shade, and knowledge of the consumer's facial features, facial skin tone, hair and eye color and lifestyle information, a method consistent with the invention may identify a recommended lipliner and blush.

Of course, lipliner and blush are only two minor examples of beauty advice. Beauty advice may additionally include any product advice that affects an appearance of the user. For purposes of the present invention, the term "product" is used broadly to refer to one or more of the following: tangible merchandise (cosmetic, non-cosmetic, accessories, or apparel), services (beauty applications, hair styling, hair cutting, hair coloring), diagnostics, beauty regimen (e.g., a combination of merchandise and/or services), opinions, instructions, and/or relevant information.

Figure 1A:
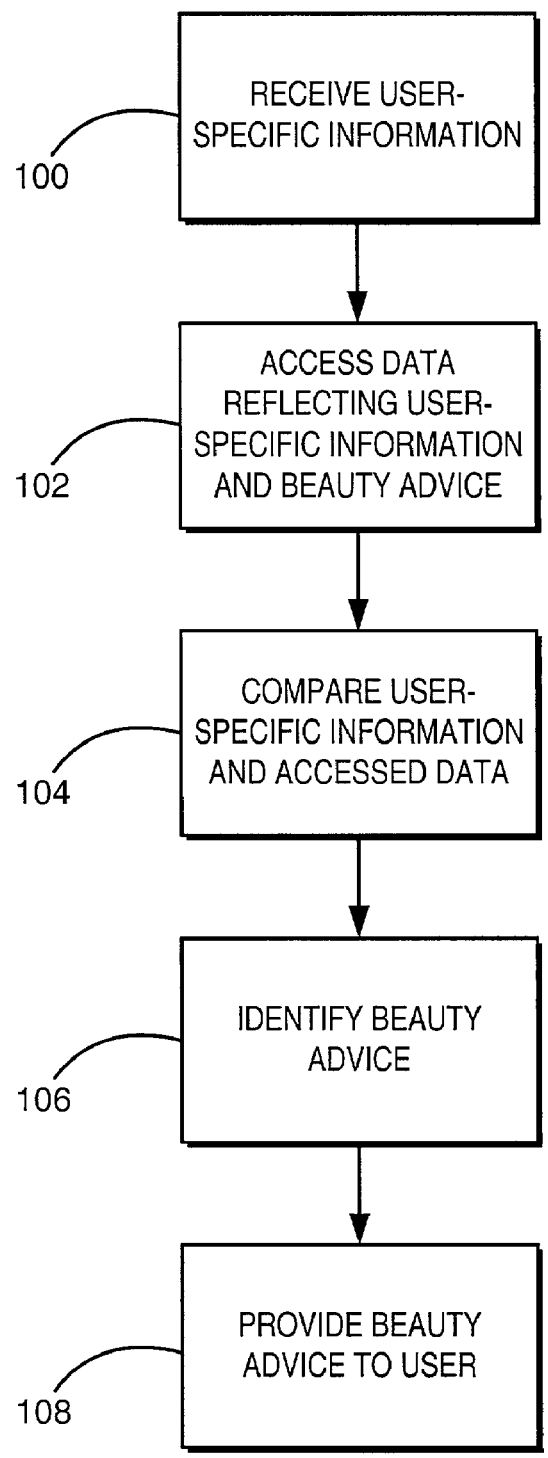
FIG. 1A is a flowchart illustrating an exemplary provision of beauty advice consistent with one aspect of the invention.

The invention in one broad sense, may be exemplified in the flow chart of FIG. 1, where user-specific information may be received at step 100. Reception of the user-specific information may be performed using one or more of a network (described below), oral communication, visual communication, written communication, physical data carrier (described below), and/or any other means capable of conveying beauty advice. Networks may include a local area network, a wide area network, a virtual private network, a dedicated intranet, the Internet, the Ethernet, a radio network, a telephony-based network, a cellular network, a wireless network, or any other mechanism enabling communication between two or more nodes or locations. Examples of a physical data carrier may include one or more of paper stock, an electronic data carrier, and a computer screen.

The user-specific information may be organized into categories, such as personal information, identifications of user-specified products, etc. Personal information may include demographics, skin and body conditions (e.g. skin type, skin texture, skin tone, wrinkles, hair color, hair style, hair condition, eye color, etc.), age, facial features, purchase history, cosmetic color, allergy information, climate information, lifestyle information, product preferences, fashion preferences, prior purchases, prior expressed interest, and/or prior browsing patterns. It should be noted that the term "user-specific information" is not necessarily related to any particular user. In this regard, the present document uses the term subject-specific information interchangeably with the term user-specific information and neither term is necessarily tied to a particular individual engaging in a particular activity.

Consistent with the invention, a method may also include accessing a data structure containing information reflecting relationships between categories of user-specific information and beauty advice, as illustrated at step 102 in FIG. 1. Data reflecting relationships may be directly from, derived from, and/or surveyed from consumer preferences and/or expert advice. The data may include information characterizing a plurality of products, information regarding the physical, ethical, physiological, biological, and aesthetic properties of the products, and/or information about suitability of combining some of the products. Ethical properties may include information indicating whether the products are tested on animals, kosher, made in the United States of America, made at a certain area location, biodegradable, made with unionized labor, contributing donations to Green Peace, contributing donations to non-profit organizations, etc. Suitability information may be maintained on less than a universe of all combinations of products. An artificial intelligence may be used to identify combinations of products not directly maintained. Information characterizing the products may include cosmetic color, inter-cosmetic compatibility, and other characteristics.

A data structure may include a read-only memory (ROM) device, random access memory (RAM) device, tape, disk drive, optical storage device, magnetic storage device, redundant array of inexpensive disks (RAID), organic storage media, computer code, constructs derived from computer code, and/or any other mechanism capable of containing information.

A method consistent with the invention may further include comparing, using an artificial intelligence engine, the received user-specific information with the accessed data, as illustrated at step 104. Comparing may include determining the appropriateness of pieces of the accessed data for the user based on the user-specific information using artificial intelligence.

"Artificial intelligence" is used herein to broadly describe any computationally intelligent systems that combine knowledge, techniques, and methodologies. An AI engine may be any system configured to apply knowledge and that can adapt itself and learn to do better in changing environments. Thus, the AI engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. Employing any computationally intelligent techniques, the AI engine may learn to adapt to unknown and/or changing environment for better performance.

Consistent with the invention, a method may additionally include identifying, using an artificial intelligence engine, beauty advice determined by the artificial intelligence engine to be related to the user-specific information, as illustrated at step 106. The determination may involve using artificial intelligence in manners described later herein.

A method may optionally include providing identified beauty advice to a user, as illustrated at step 108. Provision of the beauty advice may be performed using any of the mechanisms and methods described above for reception of user-specific information. In a broader sense, rather than directly providing the beauty advice to the user, the provision might involve sending the beauty advice to another party who may complete the provision to the user. For example, company ABC may prepare a printed report containing the beauty advice and company XYZ may send the report to the user.

Figure 1B:
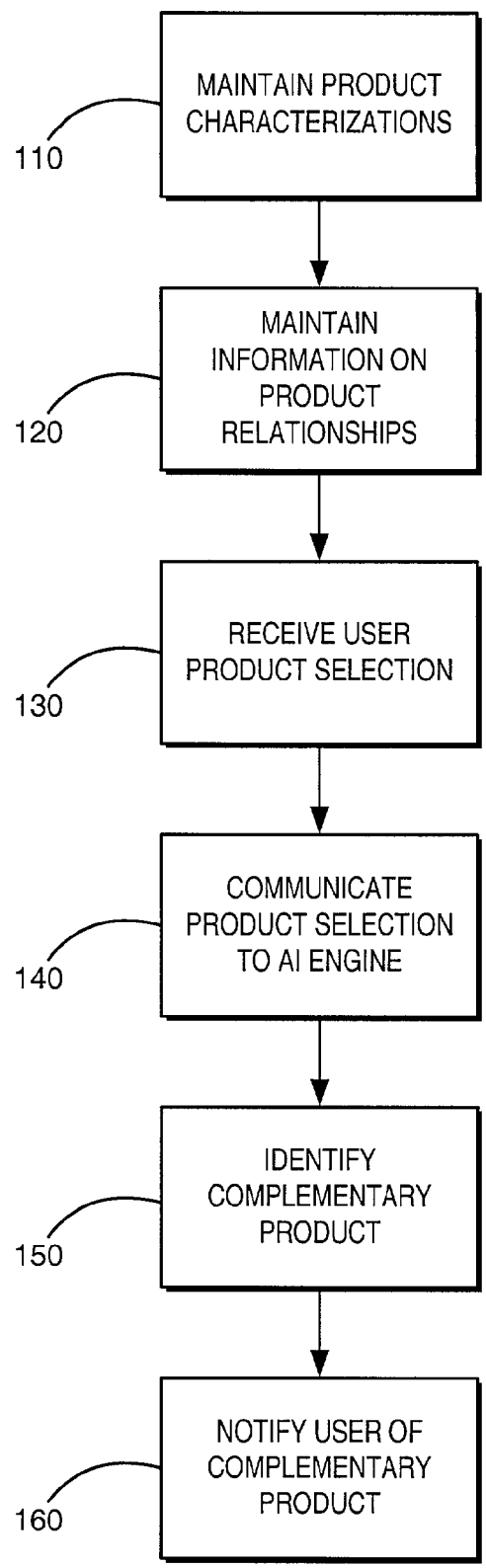
FIG. 1B is a flowchart illustrating an exemplary provision of complementary product recommendations consistent with one aspect of the invention.

The invention in another sense, may be exemplified in the flow chart of FIG. 1B, where characterizations of products may be maintained at step 110 and information relating to relationships between products may be maintained at step 120. Forms of the word "maintain" are used broadly to include gathering, storing, accessing, providing access to data, or making data available for access either directly or indirectly. For example, those who maintain information include entities who provide a link to the site of a third party where product characterizations may be stored. Further, maintained "information" may include, for example, product information reflecting complementary nature of two or more products, or the suitability of combining or using two or more products. Such information may be obtained in a number ways, including consumer experience, expert advice, and/or through an artificial intelligence (AI) engine training process as described later herein.

At step 130 in FIG. 1B, a product selection may be received from a user (e.g., consumer). Thereafter, and as will be discussed later in greater detail, the product selection may be communicated in step 140 to an artificial intelligence engine. At step 150, an AI engine may identify at least one recommended product, and the user may be notified of the recommended product at step 160.

As is discussed later in greater detail, recommended product selection may include a text or icon-based recommendations and/or may include graphical displays of the products in use on an image of a human likeness. For example, as illustrated in FIG. 2, after a user selects ABC's Ruby Red lipstick, the AI engine may generate a list of recommended products for purchase, wherein the recommended products may complement the selected ABC's Ruby Red lipstick. As illustrated in FIG. 3, the initial product selection may be displayed on an image 301. Image 301 may be a previously captured image of the user, or may be an image of a model. Techniques, systems, and methods for capturing user images are discussed in a concurrently filed U.S. application Ser. No. 10/024,495 titled Feature Extraction in Beauty Analysis, which is incorporated herein by reference.

In one embodiment, the identification of a recommended product may also be based on product characteristics, user preferences, populational data, and/or expert advice. The populational data may include preference information of a host of individuals with varying attributes, demographics, or other characteristics. Thus, populational trends may be identified and used in the recommendation process. The recommended product may also be chosen based on aesthetic, physiological, biological, ethical, and/or physical compatibility.

Figure 4:
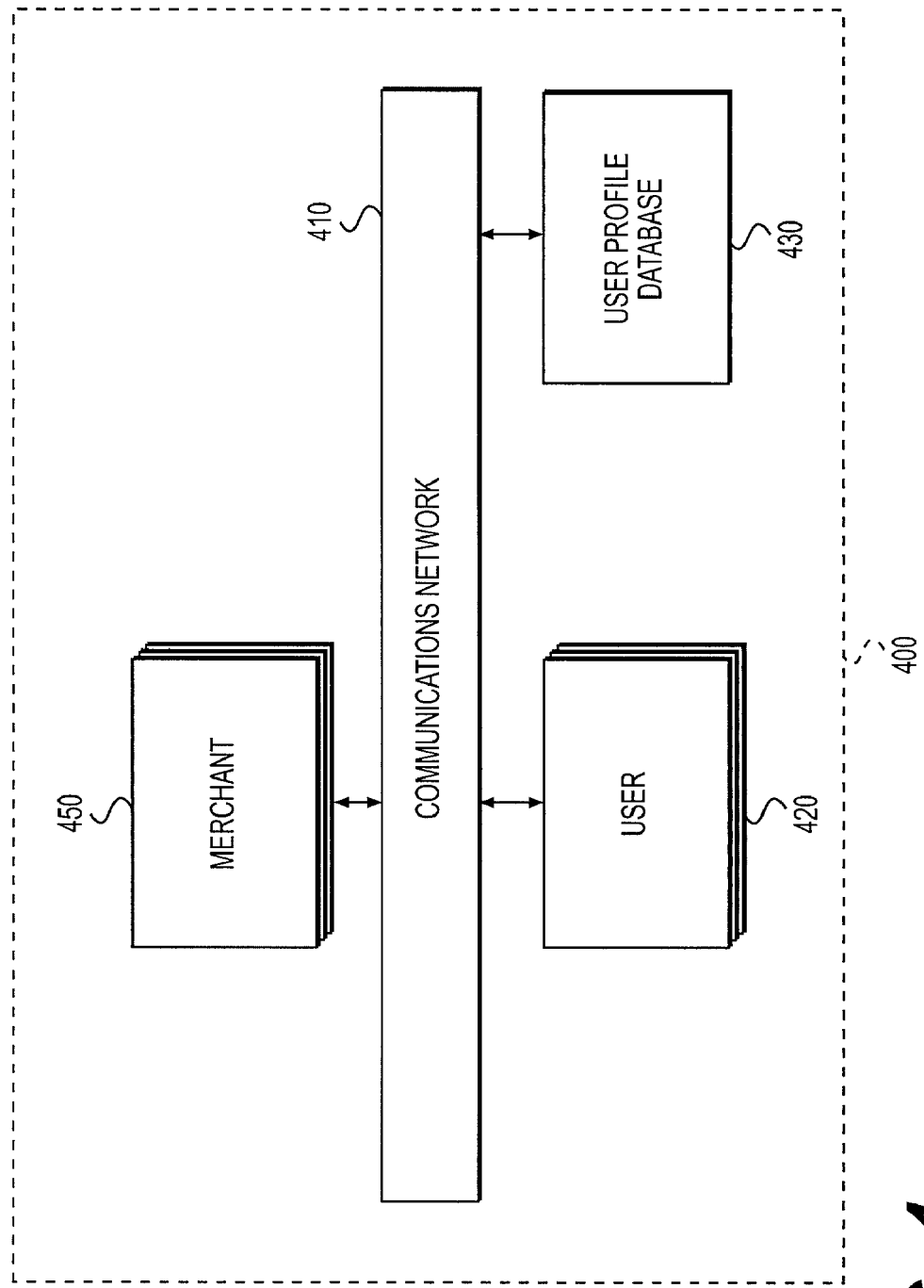
FIG. 4 is a schematic diagram of an exemplary system environment consistent with the invention.

FIG. 4 illustrates an exemplary system environment in which the invention may be implemented. For purposes of the present invention, a system 400 may be contained in a stand-alone device (e.g., a computer or a kiosk) or may be distributed over a network. For explanatory purposes, system 400 will be described in a network environment. In the network embodiment, system 400 may include a communications network 410, one or more user nodes 420, a user profile database 430, and one or more merchant nodes 450. Although it is to be understood that multiple user and merchant nodes are contemplated within the scope of the invention, for explanatory purposes only a single user node 420 and merchant node 450 are illustrated in the drawings and described herein.

Communications network 410 may represent any type of network as described above. Further, any suitable combination of wired or wireless components and systems may be incorporated into communications network 410.

User node 420 may include a data processor or a computer configured with a network browser. A user may access communications network 410 to browse the site(s) of merchant node 450. For explanatory purposes, the term "user" broadly encompasses anyone accessing system 400, including an individual, a customer, a consumer, or any other entity.

User profile database 430 may contain personal information about the user. For privacy purposes, user profile database 430 may be secure and separate from user node 420 or merchant node 450. In another embodiment, user profile database 430 may reside at user node 420.

Merchant node 450 may include a data processor, such as a web server, for providing information, services, and/or products. Merchant node 450 may be a computer, kiosk, a terminal, and/or other equipment capable of accessing system 400. Merchant node 450 may represent an independent retailer, a department store, a cosmetic company, a discounter, a beauty salon, a beauty supplier, a laboratory, and/or any other entity involved in commerce.

Merchant node 450 may also offer a variety of products and/or services of one brand and/or multiple brands. For example, merchant node 450 may provide information as well as offer for sale beauty products of one company as well as non-cosmetic products of the same or a different company. Merchant node 450 may alternatively contain information on competing products and/or offer competing products for sale. Merchant node 450 may further provide the user with an option to seek and obtain beauty advice. Alternatively, merchant node 450 may also provide the user with an option to affirmatively seek a recommendation of one or more products.

Figure 5:
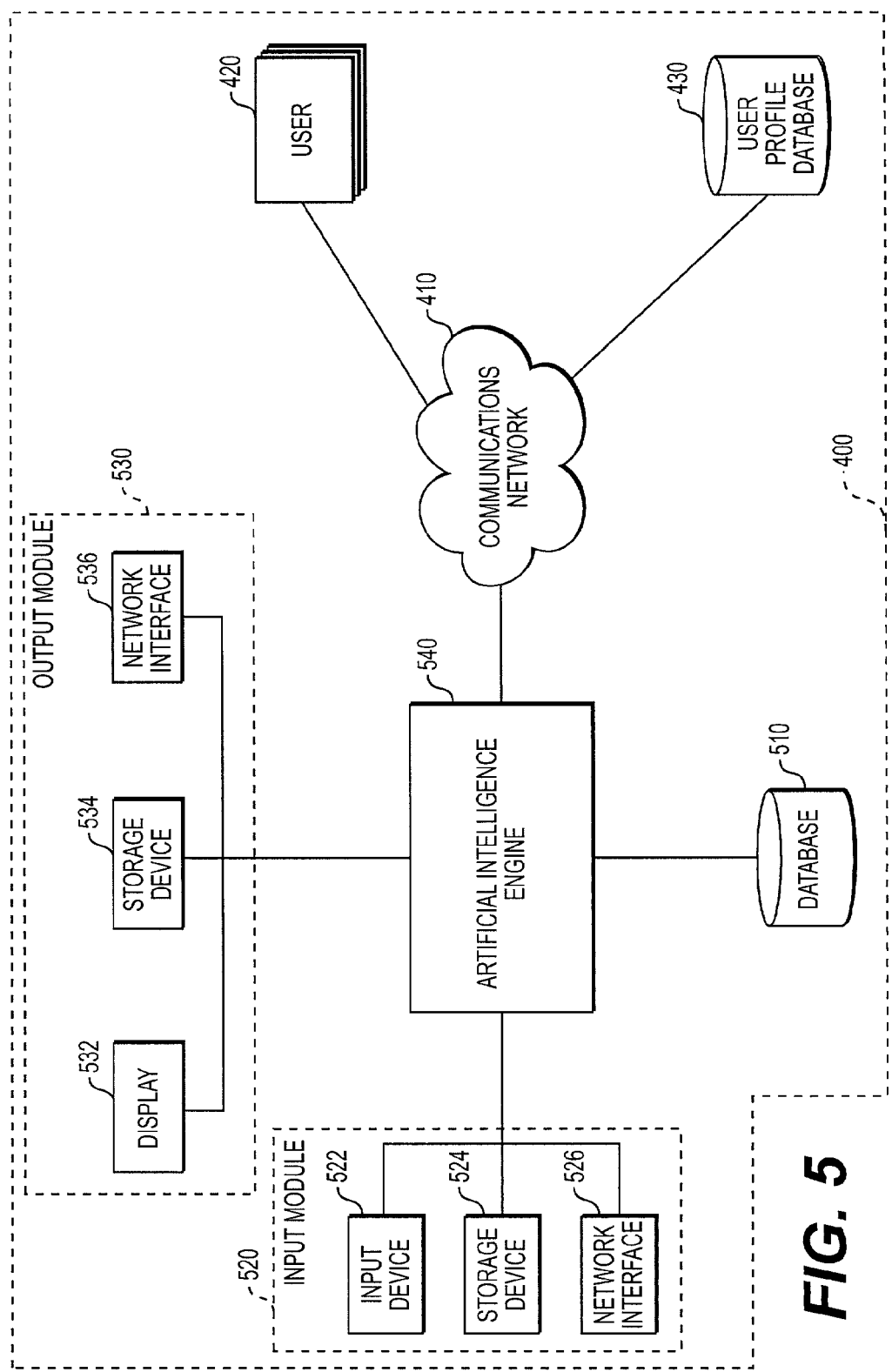
FIG. 5 is a schematic diagram of another exemplary system environment consistent with the invention.

FIG. 5 illustrates another exemplary system environment in accordance with an embodiment of the invention. As shown in FIG. 5, system 400 may include communications network 410, user node 420, user profile database 430, database 510, input module 520, output module 530, and artificial intelligence engine 540.

Database 510 may contain a variety of information for analysis and computation by AI engine 540. For example, database 510 may contain information about products and services as well as expert advice. Database 510 may be a memory location at merchant node 450 or memory location separate from merchant node 450.

Input module 520 may be implemented with a wide variety of devices for receiving information, and may include an input device 522, a storage device 524, and a network interface 526. Input device 522 may be, for example, a keyboard, a mouse, a disk drive, a telephone, a scanner, a microphone, a web cam, and/or any other suitable input mechanism for conveying information to AI engine 540.

Likewise, storage device 524 may be implemented with a wide variety of systems, subsystems, and/or devices for providing memory or storage, including one or more of the following: read-only memory (ROM) device, random access memory (RAM) device, tape, disk drive, optical storage device, magnetic storage device, redundant array of inexpensive disks (RAID), organic storage media, and/or any other mechanism capable of providing storage or memory.

Network interface 526 may facilitate an exchange of data between communications network 410 and AI engine 540. Network interface 526 may also exchange data between input module 520 and AI engine 540. In one embodiment, communications network 410 may permit a connection to at least one or more of the networks previously described or any other mechanism for enabling communication between two or more nodes or locations and connectable to input module 520.

Output module 530 may be implemented with a wide variety of devices for providing information, and may include a display 532, a storage device 534, and a network interface 536. Display 532 may be any output device, for example, a cathode ray tube (CRT), a liquid crystal display (LCD), and/or a printing device. Storage device 534 may be similar to storage device 524. Network interface 536 may exchange data between communications network 410 and AI engine 540. Network interface 536 may also exchange data between output module 530 and AI engine 540. In some aspects, network interface 536 may be similar to network interface 526.

In one embodiment, AI engine 540 may include a data processor, a personal computer, and/or a mainframe for performing various functions and operations. AI engine 540 may be implemented, for example, by a general purpose computer or a data processor selectively activated or reconfigured by a stored computer program, or may be a specially constructed computing platform for carrying out the features and operations described herein. Moreover, AI engine 540 may be implemented or provided with a wide variety of components or systems, including one or more of the following: central processing units, co-processors, memories, registers, and/or other data processing devices and subsystems.

Figure 6:
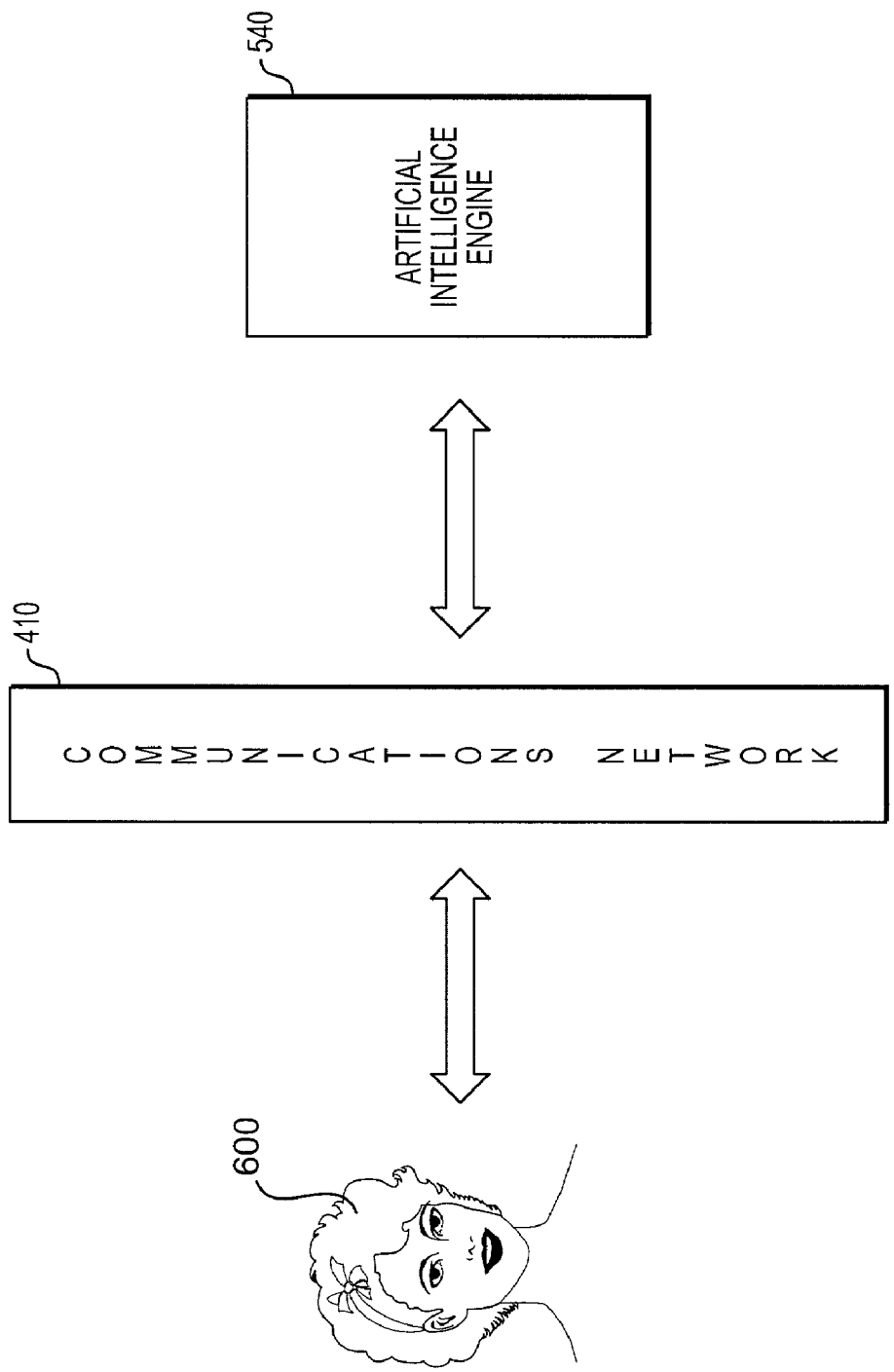
FIG. 6 is a schematic diagram of an overview of an exemplary user interaction consistent with the invention.

FIG. 6 illustrates an overview of a user interaction with AI engine 540. In a broad sense, a user 600 may interface with AI engine 540 through communication network 410 to obtain information on products and services recommended for a user-selected product. For purposes of the present invention, the user may be at any location, including user node 420 or merchant node 450.

Figure 7:
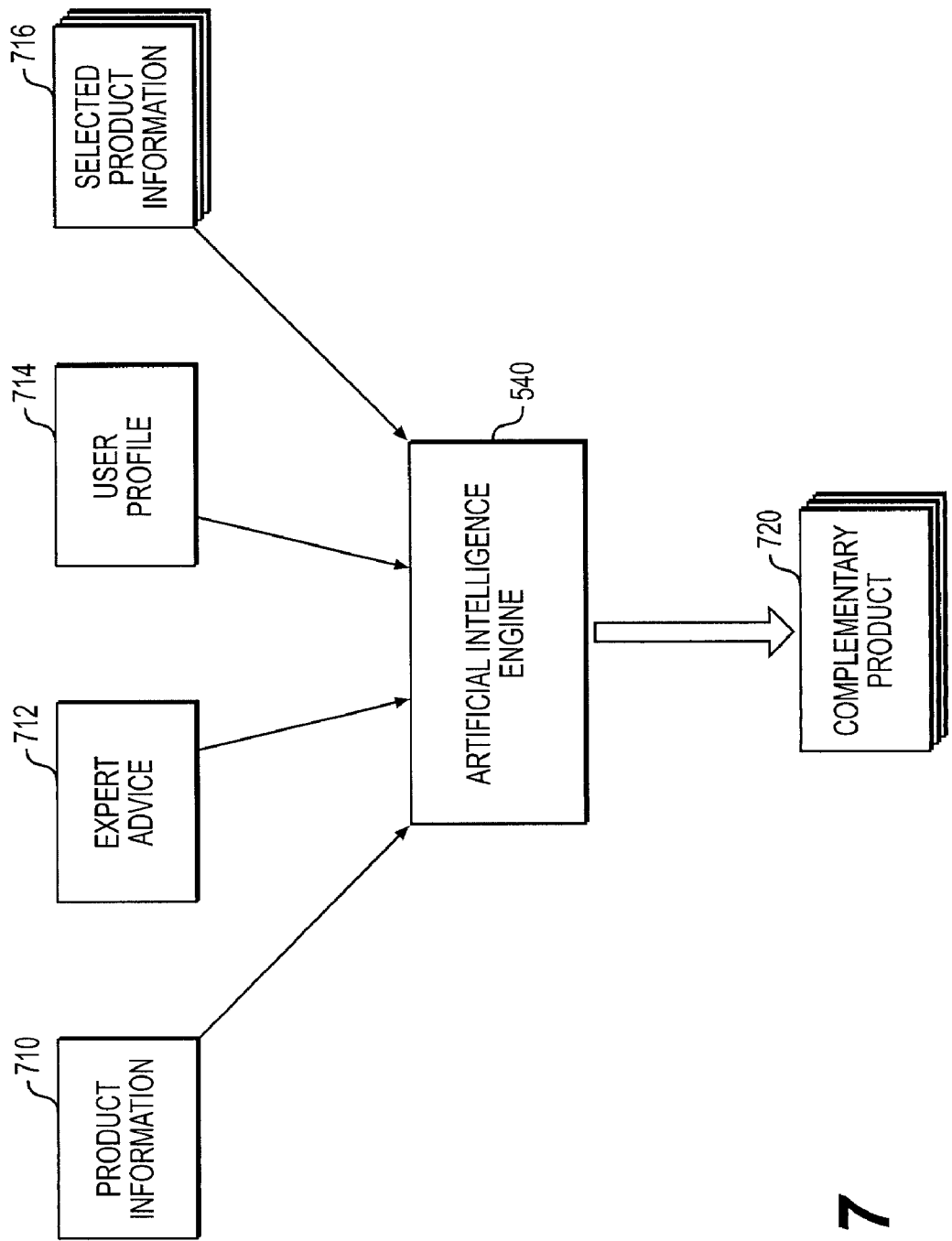
FIG. 7 is a schematic diagram of an overview of an aspect of the invention for providing recommendations of a complementary product.

FIG. 7 illustrates, in general, one embodiment of AI engine 540. AI engine 540 may analyze, for example, one or more input information: product information 710, expert advice 712, user profile 714, or selected product information 716. Expert advice 712 may include suggestions from a beauty professional, doctor, scientist, and/or any other person knowledgeable about beauty products. User profile 714 may include information related to physical characteristics, lifestyle, family history, vocation, environment, genes, mailing address, and/or any other information personal to the user. Product information 716 may include one or more of product name, indication(s), brand, cost, color, price, ingredients, description, applicable uses, promotions, and/or procedure for use or any other relevant knowledge related to or identifying the product. AI engine 540 may analyze any one or more of the input variables to identify one or more recommended products 720. The recommended products may complement a user-selected product. Product information 710 and expert advice 712 may be maintained at any convenient location such as database 510, merchant node 450, or a portable storage medium.

According to one aspect of the invention, AI engine 540 may recommend a product complementary to a product selected by a user. Complementary product 720 may be any product as previously described. Moreover, for purposes of this invention, the user may access AI engine 540 from any location, including user node 420 or merchant node 450.

FIG. 8 is a table illustrating exemplary product information 710 consistent with the invention. A product, for example, may have associated with it information relating to one or more of the following characteristics: the type of product (e.g., skincare, makeup, hair care, accessories, apparel), type of makeup (e.g., lipstick, foundation, or eye shadow), color (e.g., red, rust, brown, or purple), compatible skin type (e.g., dry, oily, or combination), compatible skin tone (e.g., light, medium, or dark), compatible eye color (e.g., blue, green, or brown), compatible hair color (e.g., blond, brown, or black), inter-cosmetic compatibility (e.g., products E, F, or G), and/or compatibility of cosmetic and non-cosmetic products (products X, Y, and Z). Product information 710 may contain one or more of the aforementioned characteristics and/or information on other features.

Figure 9:
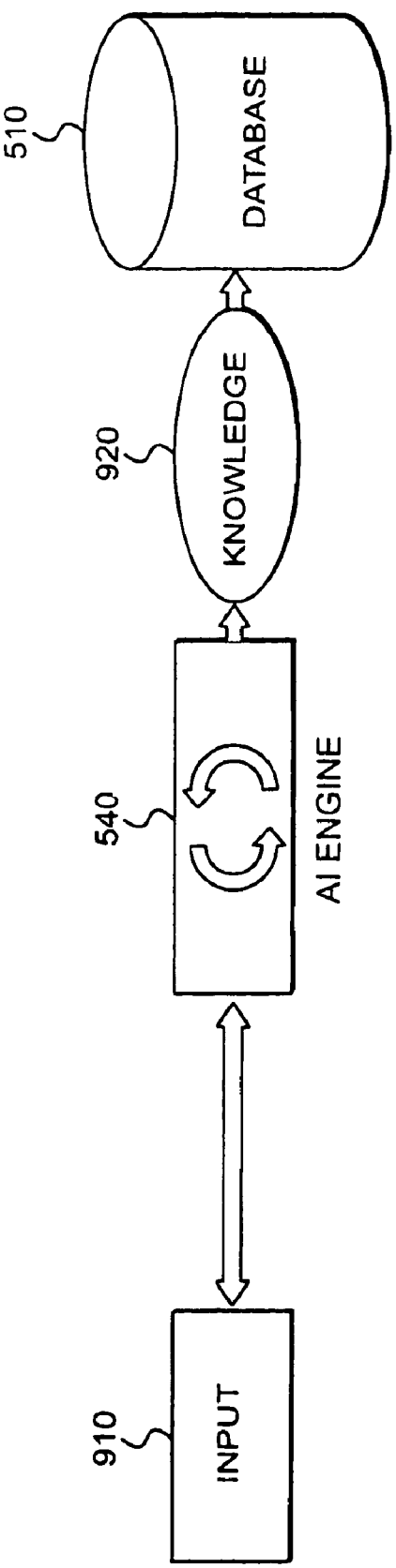
FIG. 9 is a first schematic diagram of an exemplary artificial intelligence (AI) engine consistent with the invention.

FIG. 9 is an overview of an exemplary AI engine 540 based on neural networks consistent with one aspect of the invention. AI engine 540 may be trained based on input 910. Input 910 may include any information, including product information 710, expert advice 712, user profile 714, and/or data based on sensory perceptions. Using input 910, AI engine 540 may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, and/or recording learning.

As a result of the training, AI engine 540 may learn to modify its behavior in response to its environment, and obtain knowledge 920. Knowledge 920 may represent any information upon which AI engine 540 may determine an appropriate response to new data or situations. Knowledge 920 may represent, for example, relationship information between two or more products. Knowledge 920 may be stored in any form at any convenient location, such as database 510.

Since AI engine 540 may learn to modify its behavior, information describing relationships for a universe of all combinations of products may not need to be maintained by the AI engine 540 or any other component of the system 400. The AI engine 540 may adapt and determine combinations of products and complementary product associations after an individual selects a product(s) for which suitability of combining information is not directly maintained.

As previously mentioned, for purposes of the present invention, product information 710 may be directly maintained by system 400 or indirectly maintained through a third party service. A third party service may be any entity or individual, which is not represented by any part of system 400, but provides services, products, and/or data to entities represented by any part of system 400. If a third party service maintains product information 710, such information may be provided for use by system 400 at any one time. Alternatively, the relationship may be dynamic with the third party system and may provide updates on a regular basis. The third party may provide product information 710 on a storage medium or through electronic transmission.

Figure 10:
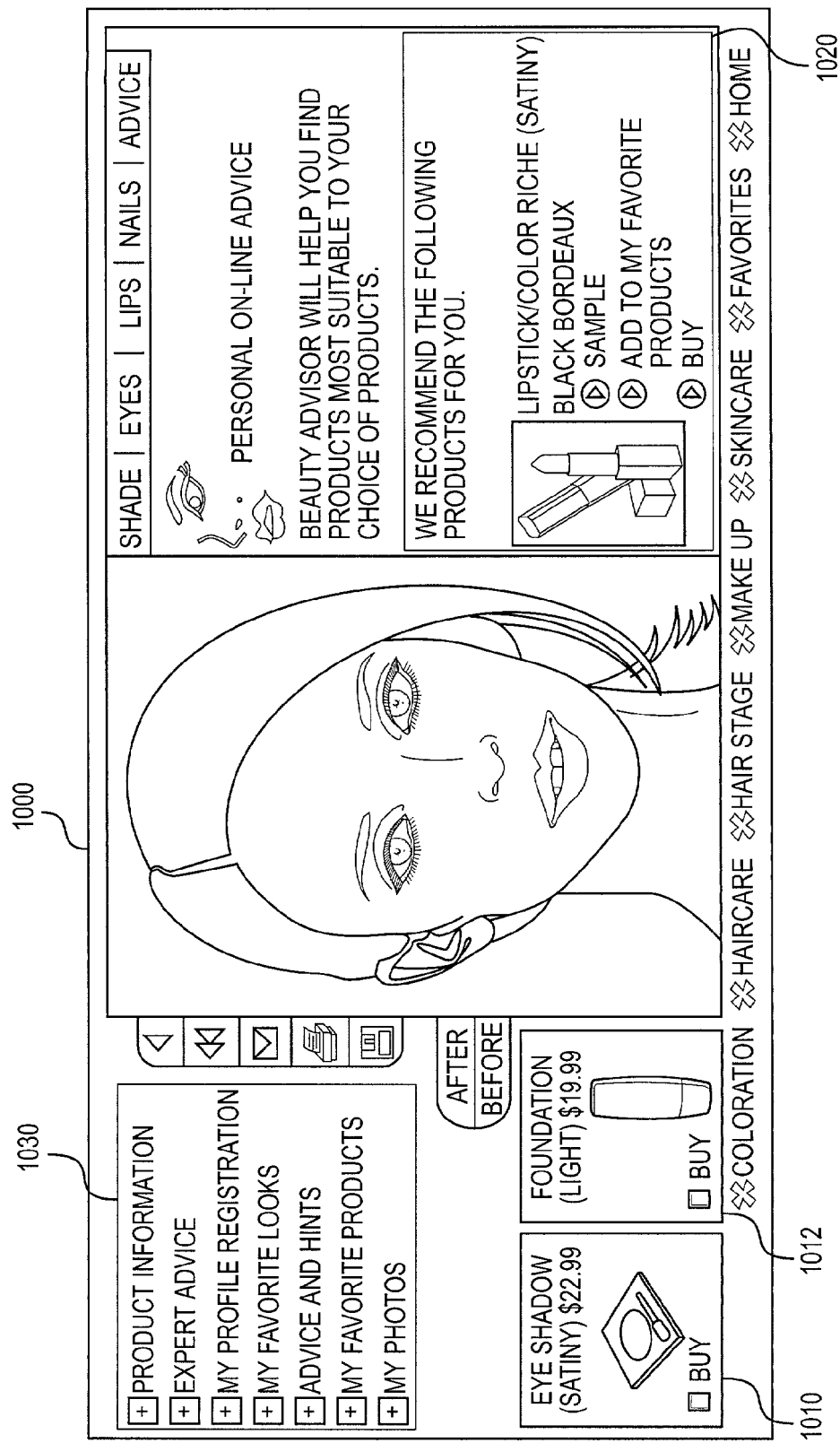
FIG. 10 is an exemplary menu display consistent with one aspect of the invention.

FIG. 10 illustrates an exemplary menu display 1000 related to recommended product selection according to one aspect of the invention. In one embodiment and with reference to FIG. 4, a user may connect to merchant node 450 through user node 420. Alternatively, the user may also access system 400 directly from merchant node 450. Once the user accesses merchant node 450, either directly or indirectly through another site, a user may access a screen such as display 1000. To obtain more information about a product or to purchase the product, the user may make a selection by simply clicking on a product or by checking an appropriate box. User selection may be a basis for selected product information 716.

In display 1000, the user may browse or select a product for informational purposes or for purchase. For example, the user may select eye shadow 1010 or foundation 1012. If the method of FIG. 1B is implemented through system 400 of FIG. 4, a user may make a product selection in step 130, and system 400 may thereafter receive selected product information 716. Selected product information 716 may be any information that identifies or is associated with the user-selected product as previously discussed.

Referring to FIG. 1B, selected product information 716 may be transmitted to AI engine 540 at step 140. Thereafter, AI engine 540 may identify at least one additional product that is complementary to the user-selected product at step 150. As mentioned above, AI engine 540 may be based on any number of computationally intelligent techniques. For illustration purposes, however, AI engine 540 will be further described using one exemplary embodiment based on neural networks.

Figure 11:
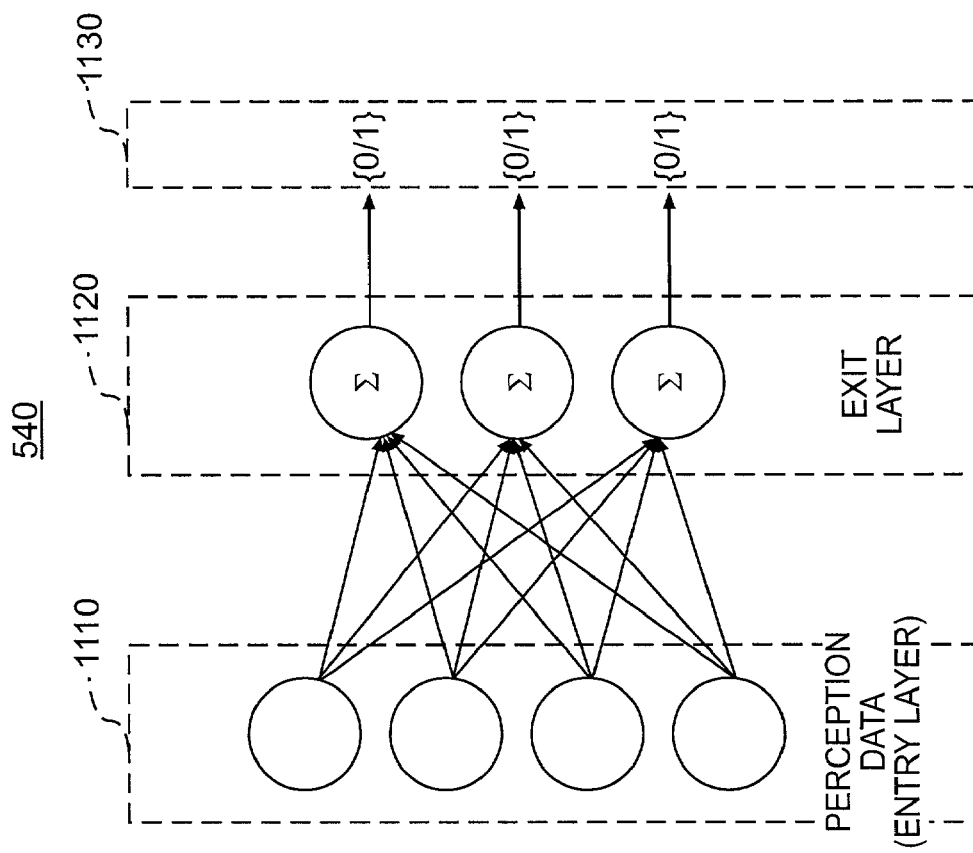
FIG. 11 is a second schematic diagram of an exemplary AI engine consistent with an embodiment of the invention.

FIG. 11 illustrates an exemplary representation of AI engine 540 based on a neural network consistent with one aspect of the invention. On a basic level, neural networks may be based on perception, which may include any sensory information, training data set, and/or perceptrons. Thus, perception data (entry layer) 1110 may be provided to train AI engine 540. In the beauty product examples, perception data 1110 may represent a wide variety of information, including physical attributes, skin conditions, product information, user preferences, and/or expert advice. Through training, AI engine 540 may obtain exit layer 1120, which represents weighted connections of perception data 1110. Knowledge 1130 gained from exit layer 1120 may be stored at any convenient location, including database 510.

Figure 12:
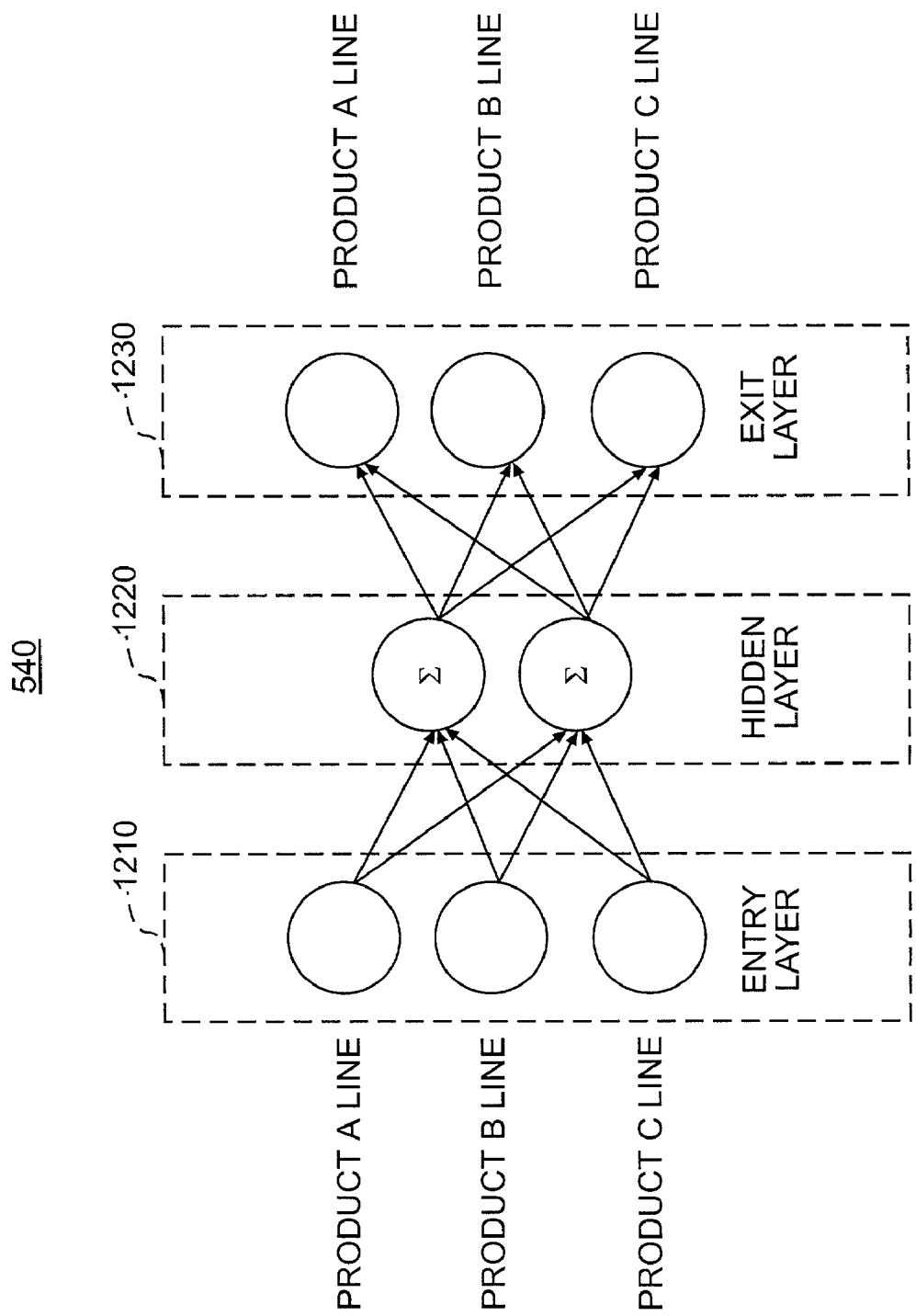
FIG. 12 is a third schematic diagram of an exemplary AI engine consistent with an embodiment of the invention.

In the neural network embodiment of AI engine 540, the connections may take place on any number of layers. For example, FIG. 12 illustrates a three-layer neural network in one embodiment of AI engine 540. An entry layer 1210 may represent a wide variety of information, including, for example, information on a line of products A, a line of products B, or a line of products C. AI engine 540 may process the information from entry layer 1210 to a hidden layer 1220, which in turn is used to generate weighted connections in an exit layer 1230.

Figure 13:
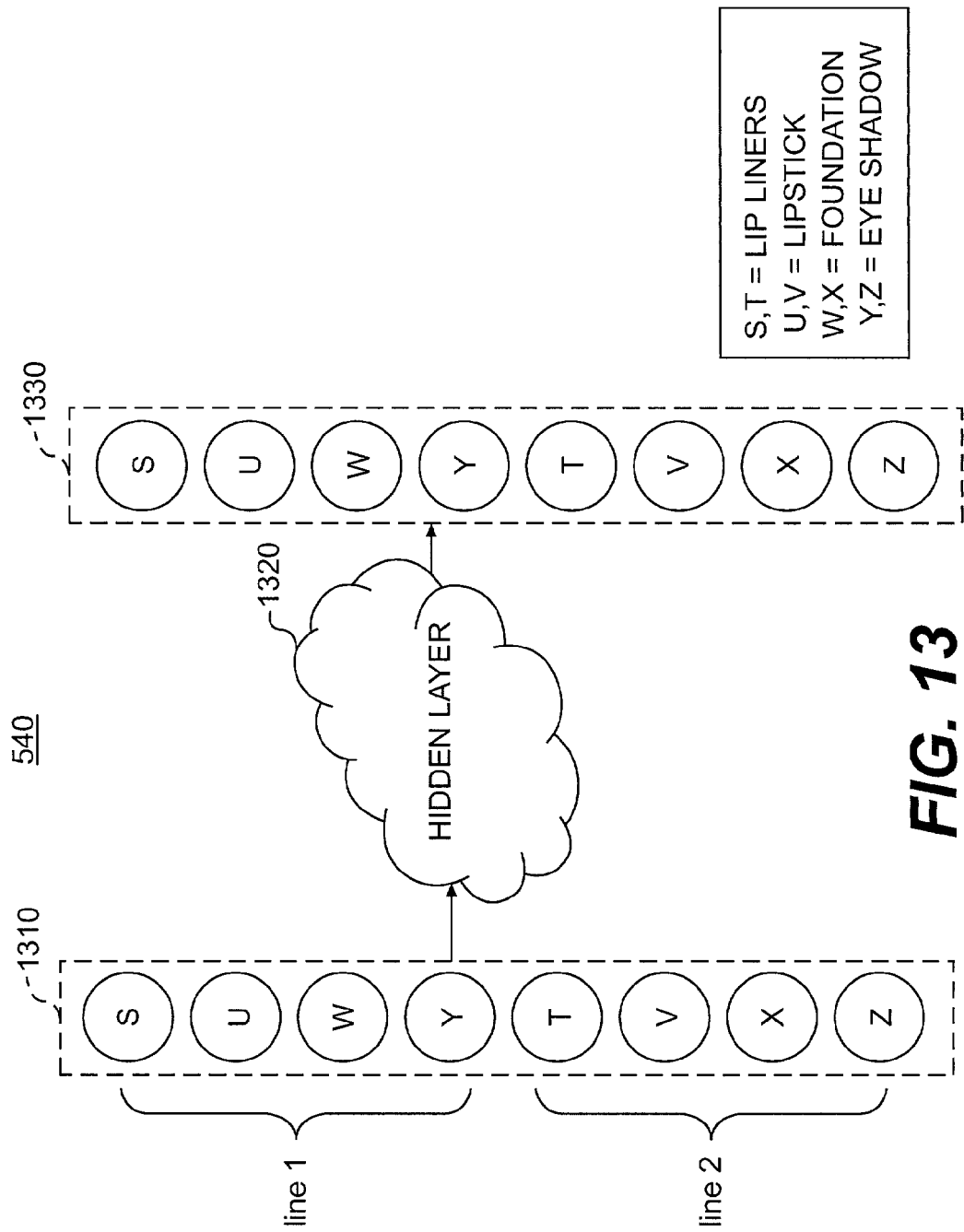
FIG. 13 is a fourth schematic diagram of an exemplary AI engine consistent with an embodiment of the invention.

FIG. 13 is yet another illustration of a neural network embodiment of AI engine 540 consistent with one aspect of the invention. Entry layer 1310 may represent any information, including beauty product information. In the present example, the line of products represent lip liners, lipstick, foundation, and/or eye shadow. The information from entry layer 1310 may be processed to a hidden layer 1320. Data from hidden layer 1320 may then be processed to generate knowledge in exit layer 1330 of AI engine 540.

Figure 14:
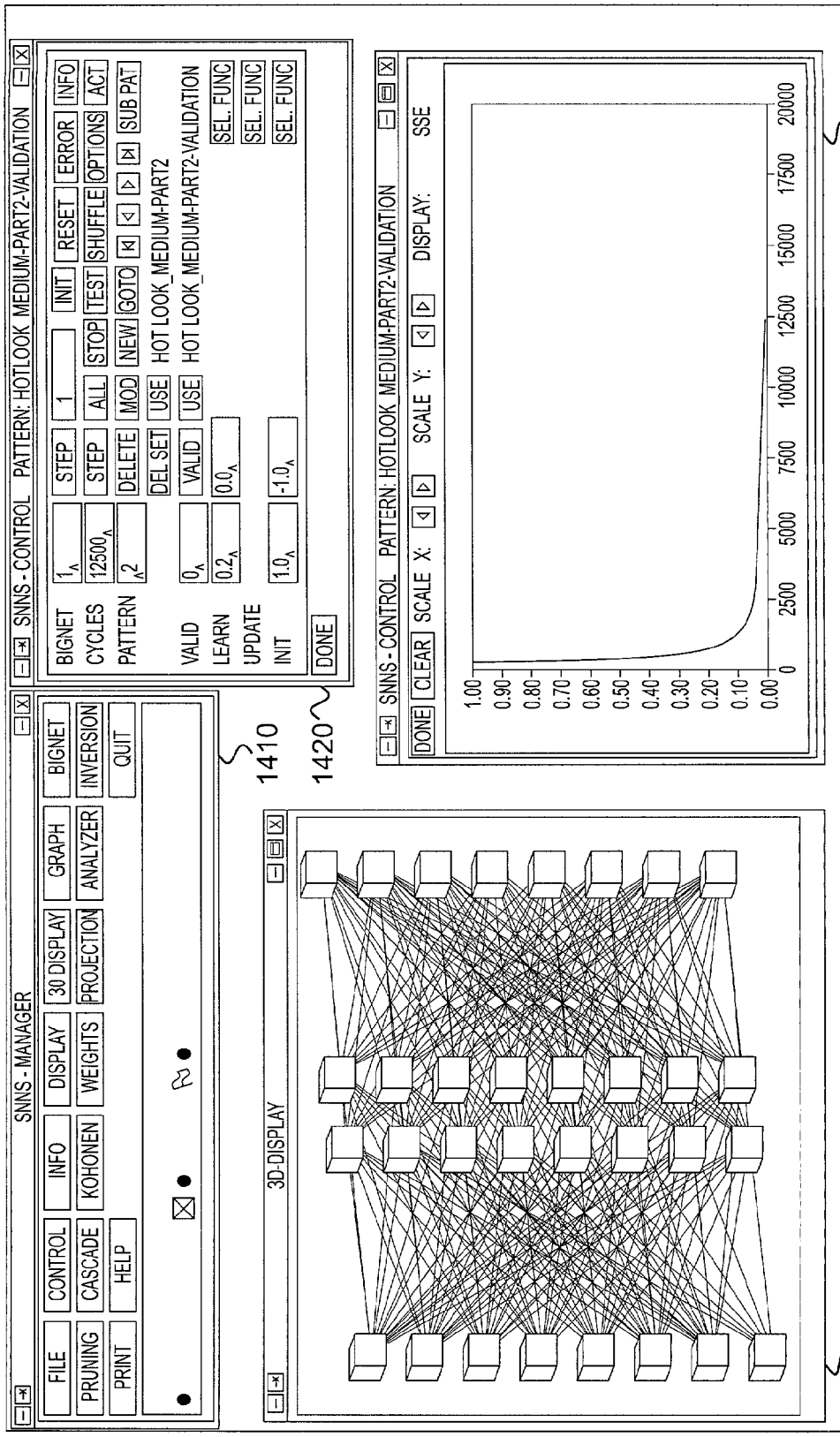
FIG. 14 is an exemplary server-side administration display for an AI engine consistent with an embodiment of the invention.

FIG. 14 is a sample screen display 1400 related to one embodiment of AI engine 540 consistent with one aspect of the invention. Manager 1410 may contain various control options for managing AI engine 540. For example, control options may include one or more of the following control options: file, control, information, display, 3 dimensional (3D) display, graph, signet, pruning, cascading, Kohonen, weights, projections, analyzer, inversion, print, or help. Screen display 1400 may contain other windows or tool bars. A control panel 1420 may be provided for control and validation of AI engine 540. Through the use of various calibration options, AI engine 540 may adjust and improve system performance.

A 3D display 1430 may illustrate the underlying engine, in this example a neural network, in a 3D model. Also, a graphic display 1440 may illustrate the performance or underlying analysis of AI engine 540 as a Cartesian graph.

To identify a complementary product, AI engine 540 may access product information 710. In one embodiment, AI engine 540 may identify a complementary product based on product characterizations and relationships between products. In another embodiment, AI engine 540 may identify complementary product 720 based on an analysis of any combination of one or more of the following information: selected product information 716, product information 710, expert advice 712, or user profile 714.

Referring to FIG. 1B, the user may be notified of complementary product 720 at step 160. The user may be notified by any means, including a display, printer, and/or e-mail at user node 420 or merchant node 450. In the example provided in display 1000 of FIG. 10, the user selection of eye shadow 1010 may render the display of a recommended lipstick in recommended product window 1020.

In general, selected product information 716 may represent user selection of any number or type of products. Similarly, recommended product 720 may be any number or type of products. For example, the user may select two or more products, and AI engine 540 may identify one recommended product 720. Or vice versa, the user may select one product and AI engine 540 may identify two or more recommended products.

In one embodiment, selected product information 716 may include associated aesthetic characteristic. In that case, AI engine 540 may identify at least one product with an aesthetic characteristic complementary to the aesthetic characteristic of the selected product. For example, if the user selects a pink lipstick, AI engine 540 may identify a pink lip gloss that would match the lipstick. In another embodiment, the selected product may be a beauty product, and recommended product 720 may be a beauty product that aesthetically complements and is physically compatible with the selected beauty product. For example, if the user selects a pink lip stick, AI engine 540 may identify a matching pink lip gloss that aesthetically complements and matches the physical texture of the lipstick. In identifying a complementary product, the AI engine may take into account personal attributes or other information personal to the subject.

In another embodiment, the selected product and recommended product 720 may be chosen from at least one of cosmetics, apparel, and/or accessories. In yet another embodiment, a non-cosmetic recommended product 720 may be selected based on a selected beauty product. Thus, if the user selects a pink lipstick, the AI engine may identify a matching scarf, or vice versa. Still further, in another embodiment, a cosmetic recommended product 720 may be selected based on a selected beauty product. In yet another embodiment, a cosmetic recommended product 720 may be selected based on a selected non-cosmetic product.

Further, in another embodiment, the user may be presented with an opportunity to purchase the user-selected product and recommended product 720. In FIG. 10, for example, the user may have the option of buying eye shadow 1010 and recommended lipstick in recommended product window 1020. The user may be notified of a recommended product before the user completes the purchase of user-selected product. For example, in the example of FIG. 10, the user may select eye shadow 1010. Before the user completes the purchase of eye shadow 1010, the user may be notified of the recommended lipstick.

FIG. 10 also depicts an action window 1030, which provides various options for the user. The user may, for example, obtain product information, seek expert advice 712, or register user profile 714.

FIG. 15 is a table illustrating exemplary expert advice 712 according to one embodiment of the invention. Expert advice 712 may be provided by an expert beauty consultant and/or specialist, either based on their expertise and/or based on data gathered from user surveys and/or questionnaires. Expert advice 712 may include, for example, relationships between products (e.g. inter-product compatibility), relationships between products and physical human attributes, recommended treatments for certain beauty conditions, and/or color compatibility tips. Expert advice 712 is not limited to the afore-mentioned examples and may include other opinions and/or recommendations of persons with beauty knowledge.

Figure 16:
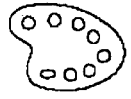
FIG. 16 is an exemplary display of a user profile questionnaire consistent with an embodiment of the invention.

FIG. 16 illustrates an exemplary user profile 714 according to one embodiment of the invention. User profile 714 may include personal and/or demographic information of the user such as one or more of name, age, body conditions (e.g., skin type, skin texture, skin tone, wrinkles, hair color, hair style, hair condition, eye color, allergy, and/or other special conditions), physical characteristics (e.g., facial features), demographics (e.g., region, climate, and/or lifestyle), user preferences (e.g., preferred types of products, cosmetic color, apparel color, types of accessories, brands, and/or products), and/or purchase history.

In one embodiment, a user may provide information on user profile 714 using a user profile form illustrated in FIG. 16. For purposes of the present invention, however, any mode of data entry suffices, including check boxes, textual entries, graphical input such as a color window 1722 in FIG. 17, image input (e.g. submission of captured facial image), and/or audio input. To ensure privacy, user profile 714 may be stored at a secured site, such as user profile database 430. For purposes of this invention, however, user profile 714 may be located at any location, including any location within user node 420, a portable storage medium, and/or other network location, or may be maintained in user-controlled memory, such as the user's personal hard drive associated with user node 420. A portion or all of the user profile 714 may be accessed by merchant node 450.

Figure 17:
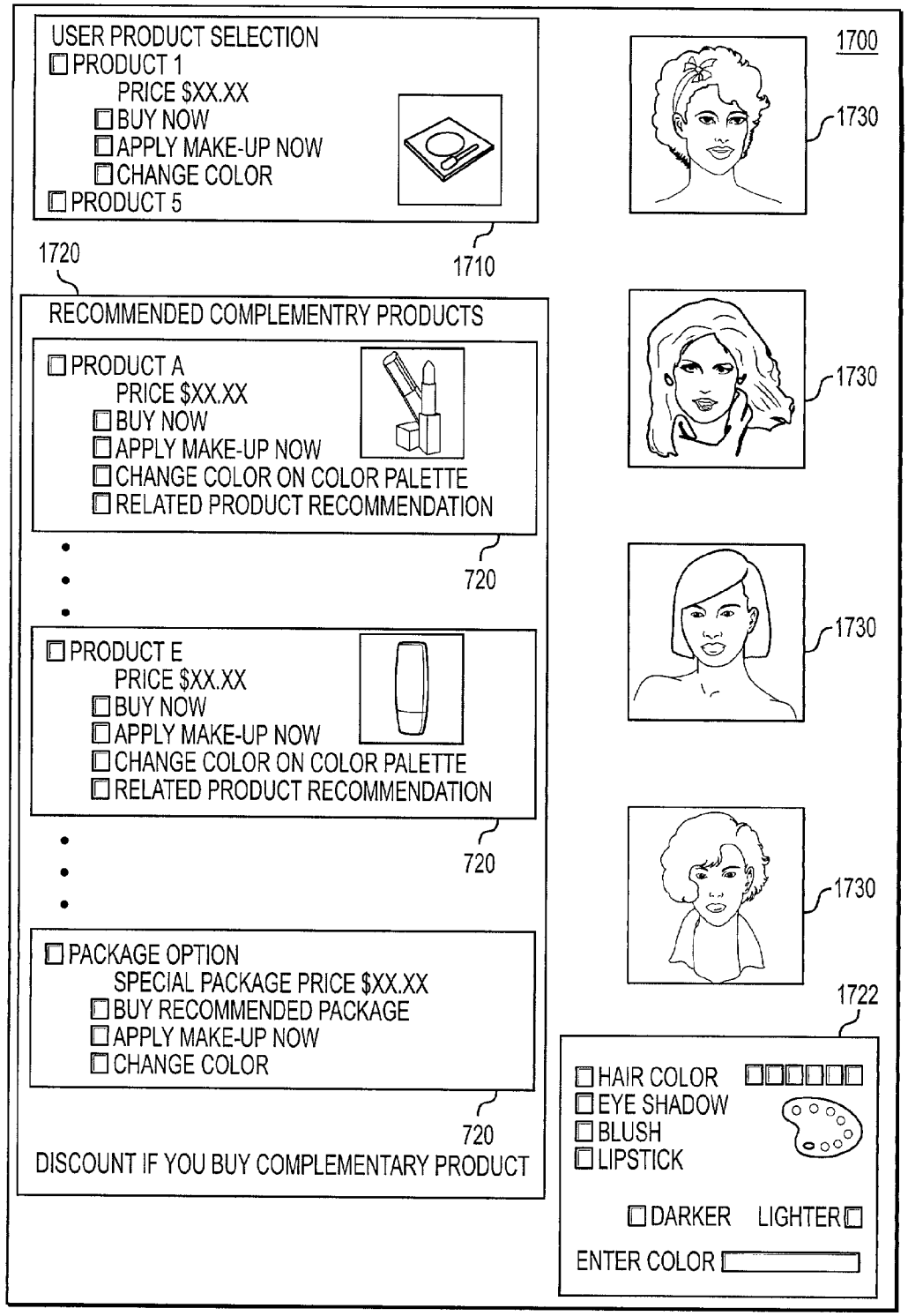
FIG. 17 is an exemplary recommended product display consistent with an embodiment of the invention.

FIG. 17 is another exemplary display related to recommended product selection according to one aspect of the invention. In one embodiment, a display 1700 may contain a user product selection window 1710 for one or more of the products the user selected. Similarly, display 1700 may contain recommended product window 1720 for one or more recommended products 720. Additionally, color window 1722 may allow the user to change the color of a selected product or recommended product 720. For example, color window 1722 may include a color bar, a color palette, textual entry, and/or a progressive color adjuster that makes the color darker or lighter.

In one embodiment of user product selection window 1710, the user may have the option of buying the selected product, applying the selected product graphically, and/or changing the color of the selected product. Any one or combination of these and other options may be provided in user product selection window 1710. In another embodiment, a plurality of the selected products may be displayed simultaneously in full. In yet another embodiment, a summary, a thumb sketch, and/or a list of the selected products may be displayed, with the option for the user to more fully display information on any selected product.

In one embodiment of recommended product window 1720, information on recommended product 720 is displayed in full for one or more of recommended products 720. In another embodiment, a summary, a thumb sketch, and/or a list of recommended product 720 may be displayed, with the option for the user to more fully display information on any recommended product 720. The list of recommended product 720 may be maintained in a data structure stored on the system 400.

Recommended products 720 may be an individual product and/or a package of products. In one embodiment, the package option may include a special discount. The discount may be applied if the user purchases an individual recommended product and/or package of recommended products with the selected product. The discount may be offered at time of payment. The discount may be used by the AI engine 540 as a sales tool to encourage sales that may not otherwise occur.

For each recommended product 720, the user may have the option of buying recommended product 720, applying graphically recommended product 720, changing the color of recommended product 720, or requesting a related product recommendation based on recommended product 720. A graphical representation of recommended product 720 may also be provided.

If the user elects to buy the selected product or recommended product 720, merchant node 450 may charge the user's registered account, bill the user later, and/or request payment information from the user. For a registered user, merchant node 450 may simply access pre-stored payment information of the user.

In another aspect of the invention, display 1700 may also provide an option to perform a visual simulation of a product. The visual simulation feature may be interesting to the user who desires to see what the product would look like when applied. For example, if recommended product 720 is a lipstick, the lipstick may be applied on the face of a model of choice 1730. The visual simulation feature may also be available for user-selected products.

However, in its broadest sense, features and principles of the present invention do not necessarily require a visual simulation of a selected product and/or recommended product. Information regarding the application of the selected or recommended product may be provided visually, textually, audibly, and/or in any other manner with or without visual simulation.

Figure 18:
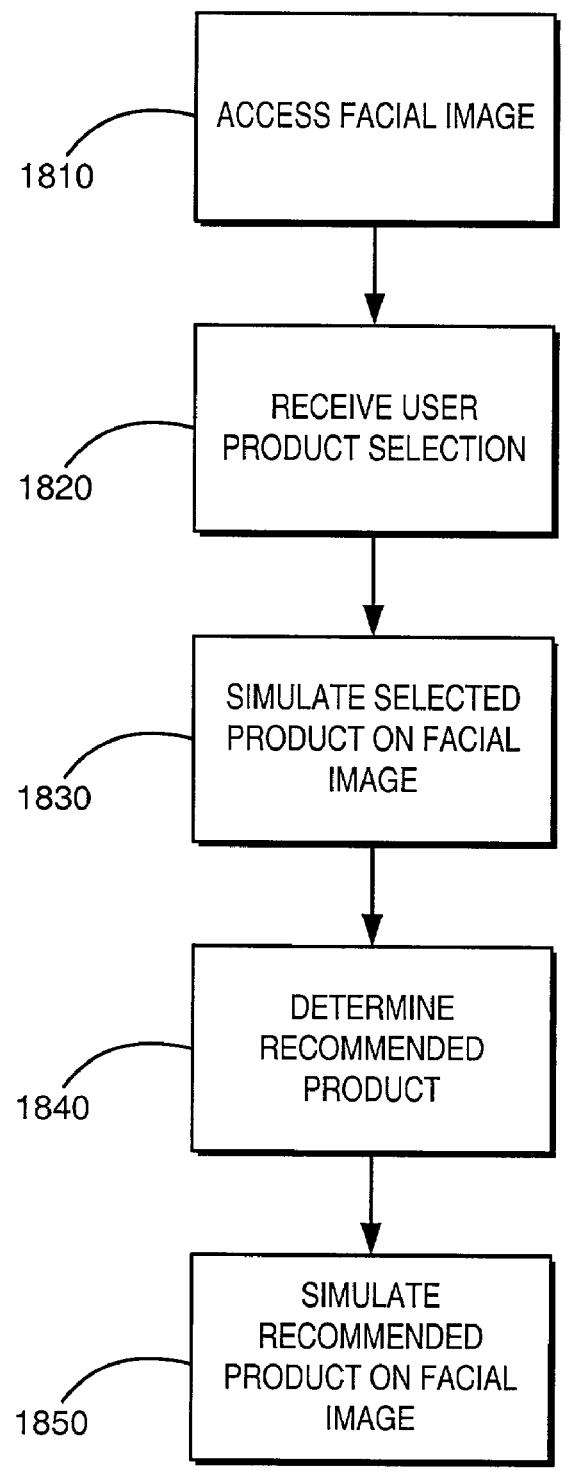
FIG. 18 is a flowchart illustrating an exemplary visual simulation according to an embodiment of the invention.

FIG. 18 is a flowchart illustrating an exemplary visual simulation according to one embodiment of the invention. As with all flowcharts contained herein, the order of the steps as presented are for exemplary purposes only and are not intended to limit the invention in its broadest sense.

As indicated in FIG. 18, regardless of system implementation details, a facial image may be accessed at step 1810. Accessing may include obtaining a facial image from a network, data structure, and/or storage medium. Examples of a network, data structure, and storage medium are previously described. Accessing may also include processing the facial image to permit simulated application of beauty product to a selected portion of the facial image as described later herein. Accessing may further include receiving the facial image. Receiving may be performed using any mechanism or method described above for reception of user-specific information.

During or after receiving the facial image, the facial image may be displayed. While the term "displaying" may include a direct act of presenting content, in a broader sense, the invention is not so limited. Specifically, as used herein, forms of the word "displaying" may include indirect acts such as providing content for transmission over a network to a display unit, regardless of whether the display unit is in the custody and/or control of the sender. "Displaying" may further include preparing content for delivery to an intermediate carrier which may then transmit the content to an end user for presentation of the content on an end user's display device. Thus, any entity in a chain of delivering information for display performs an act of "displaying" within the context of this patent. This also includes parties involved in the provision of software to facilitate facial image display. Software may include computer programs, routines, and/or any instructions implementable by computer or electronic devices. As previously described, a display may include a CRT, LCD, printing device, and/or any other information output device.

A method consistent with the invention may include receiving from the user a selection of at least one beauty product for simulated application to the facial image, such as is generally represented at step 1820 in FIG. 18. For example, the user may select a product for simulated application to a facial image such as image 1730 in FIG. 17. The product selection may be received by verbal communication, written communication, visual communication, electronic communication, and/or through previously described mechanisms such as those discussed in connection with input device 522 in FIG. 5.

A method consistent with the invention may also include simulating at least one selected beauty product on the facial image (step 1830). The user-selected product(s) may be simulated and/or displayed on the facial image using known image processing techniques at step 1830. As used herein, the term "simulating" may include an act of image processing to cause an application of a beauty product to appear on a facial image. In a broader sense, the term "simulating" may also include any act that facilitates presentation of a simulated beauty application. Such acts may include providing image processing software either physically, electronically, and/or through association with a third party who performs image processing functions. Image processing functions may include image processing techniques referred to in one or more of a series of concurrently filed applications incorporated herein by reference.

A method consistent with the invention may further include determining a recommended beauty product based on at least one selected product at step 1840. As stated above, recommended products may be complementary products identified for the user-selected products. Complementary product selection may occur using one or more of the techniques previously discussed. For example, identification of complementary products may be achieved using an artificial intelligence engine. The recommendation may be requested by the user or automatically performed, regardless of whether or not the user is seeking a recommendation. Recommendations may be provided by verbal, written, visual, or electronic communication in a manner similar to, but not limited to, a manner in which product selections are received at step 1820.

Consistent with the invention, a method may additionally include simulating at least one recommended beauty product on a facial image. At step 1850, simulation of a recommended product(s) may include modifying a facial image such that a user may obtain knowledge of how user-selected product(s) and recommended product(s) may appear when worn together or separately. Simulation on facial images may include modifying (or creating) a photograph of a model, a graphical representation of a model, a user's photograph, a graphical representation of a user, a 3-D projection of a model, a 3-D projection of a user, and/or any other representation of a user or a model. Regardless of the format, simulation may be performed on any selected portion and/or all of the facial image. Simulation of recommended products may also include concurrently simulating and/or displaying the user-selected and recommended products on a single image, sequentially simulating the user-selected and recommended products on a single image, separately simulating the user-selected and recommended products on multiple images and/or morphing images.

When implemented in an environment that includes display 1700, the user's facial image may appear in lieu of model image 1730. Or the user may have the option of selecting either the user's own image and/or a model that most closely resembles the user. In one embodiment, the user may select one of facial image 1730 by simply clicking a mouse over the image. The display of facial image 1730 may be performed by any existing and/or customized software.

With reference to FIG. 4, the user may also select, and system 400 may receive information on, a product for simulated application on facial image 1730. For example, the user may select the "apply make-up now" option in user product selection window 1710.

Merchant node 450 may visually simulate the selected product on facial image 1730. FIGS. 17 and 19 illustrate sequential exemplary displays of a visual simulation feature according to one aspect of the invention. In this example, the user selected the eye shadow from user product selection window 1710 in FIG. 17. In response, the eye shadow may be visually simulated on facial image 1730 to render a simulated image 1910.

Thereafter, merchant node 450 (FIG. 4) may determine a recommended product 720 based on the user-selected product. In one embodiment, the user may affirmatively seek a recommendation for a recommended product. For example, the user may affirmatively seek a recommendation based on one or more of brand, price, store, and/or product characteristic. The user may seek a recommendation on recommended product 720 in any manner, including activating a button. In one embodiment, the user may also choose the information to be considered in making the selection. For example, the user may choose to receive a recommendation based on one or more of product information 710, expert advice 712, user profile 714, and/or selected product information 716.

Merchant node 450 may then visually simulate the recommended product 720 on facial image 1730 (FIG. 17). As illustrated in FIG. 19, simulated image 1920 may contain the visual simulation of user-selected product and recommended product. For example, simulated image 1920 may reflect the application of user-selected eye shadow and recommended lipstick. While FIG. 19 illustrates separate before and after images, all beauty product simulation may occur on a single image, with the user having the option of viewing prior images using a back button. Alternatively, morphing techniques may be employed to illustrate contrast to the user.

In one embodiment, a list of recommended products 720 may be provided to the user and the user may select one or more products from the list. Upon selection, recommended product 720 may be simulated on facial image 1730. By way of example, the list may be derived from one or more of the following: advice of beauty experts, user preference data, populational data, and/or user purchase history.

Also, further personal information from the user may be elicited. In one embodiment, recommended product 720 may be selected based on the user-selected product and the elicited personal information.

In another embodiment, the user may be provided with one or more alternative recommended products 720. Upon identifying one or more alternative recommended products 720, merchant node 450 may provide a visual simulation of one or more alternative recommended products 720 on an image of a model or the user. For alternative recommended products 720, the visual simulation may occur sequentially or simultaneously on multiple images for comparative purposes.

FIG. 20 illustrates another embodiment of a visual simulation feature according to one aspect of the invention. In this embodiment, the visual simulation of one recommended product 720 may appear on a first simulated image 2010, while at the same time, the alternative recommended product 720 may appear on a second simulated image 2020. In another embodiment, the user may toggle between displays of the first and second or either simulated images and the unaltered image 1730. In yet another embodiment, a visual simulation of at least one recommended product 720 may be applied on an image along with a user-selected product, followed by a simulation of an alternative recommended product 720 with a user-selected product.

Alternatively, visual simulation may occur for one or more of the user-selected products in combination with visual application of one or more recommended products 720. The visual simulation of multiple products, for example, a user-selected lipstick and complementary eye shadow, may be displayed simultaneously on one image, sequentially, or under manual control such as a user toggle switch.

In another embodiment, the user may change the color of the product before or after the initial visual simulation, as illustrated in FIG. 17. In one case, for example, after evaluating the initial application of recommended product 720 in red, the user may desire to see the visual application of the same recommended product 720 in a different color. Thus, the user may choose a different color using any input methods through color window 1722. In one embodiment, the user may choose to change the color of one or more products on a facial image.

In yet another embodiment, the user may request a recommendation on a product related to recommended product 720. Alternatively, the user may seek a recommendation on a product related to any combination of one or more recommended products 720 and a user-selected product. For example, if recommended product 720 is a red lipstick, the user may receive a recommendation of a related product, e.g., a matching red lip liner. In one embodiment, the user may trigger a simulation of the related recommended product. Additionally, the user may also choose to change the color of the related recommended product before or after the visual simulation.

Figure 21A:
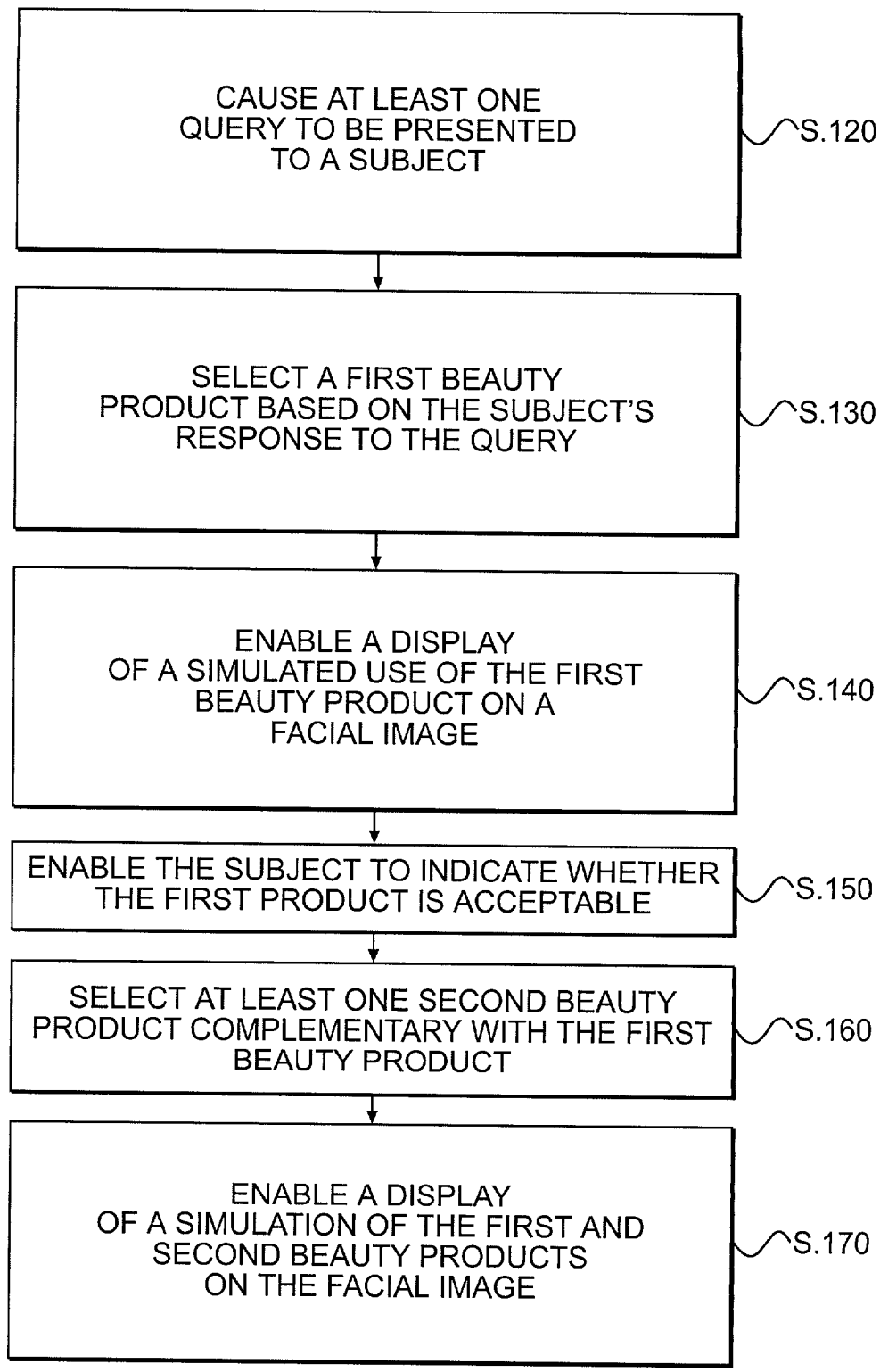
FIG. 21A is a flowchart of an exemplary method for recommending at least one complementary beauty product consistent with the present invention.

Another embodiment consistent with features and principles of the invention may include a method of recommending at least one complementary cosmetic product, as illustrated in a flowchart of FIG. 21A. As explained in more detail below, such a method may involve causing at least one query to be presented to a subject (S.120); selecting a first beauty product based on the subject's response to the query (S.130); enabling a display of a simulation of the first beauty product applied on a facial image (S.140); and enabling the subject to indicate whether the first beauty product is acceptable (S.150). When the first product is indicated as being acceptable, the method may further include selecting at least one second beauty product complementary with the first beauty product (S.160); and enabling a display of a simulation of the first and second beauty products applied on the facial image (S.170).

Figure 22:
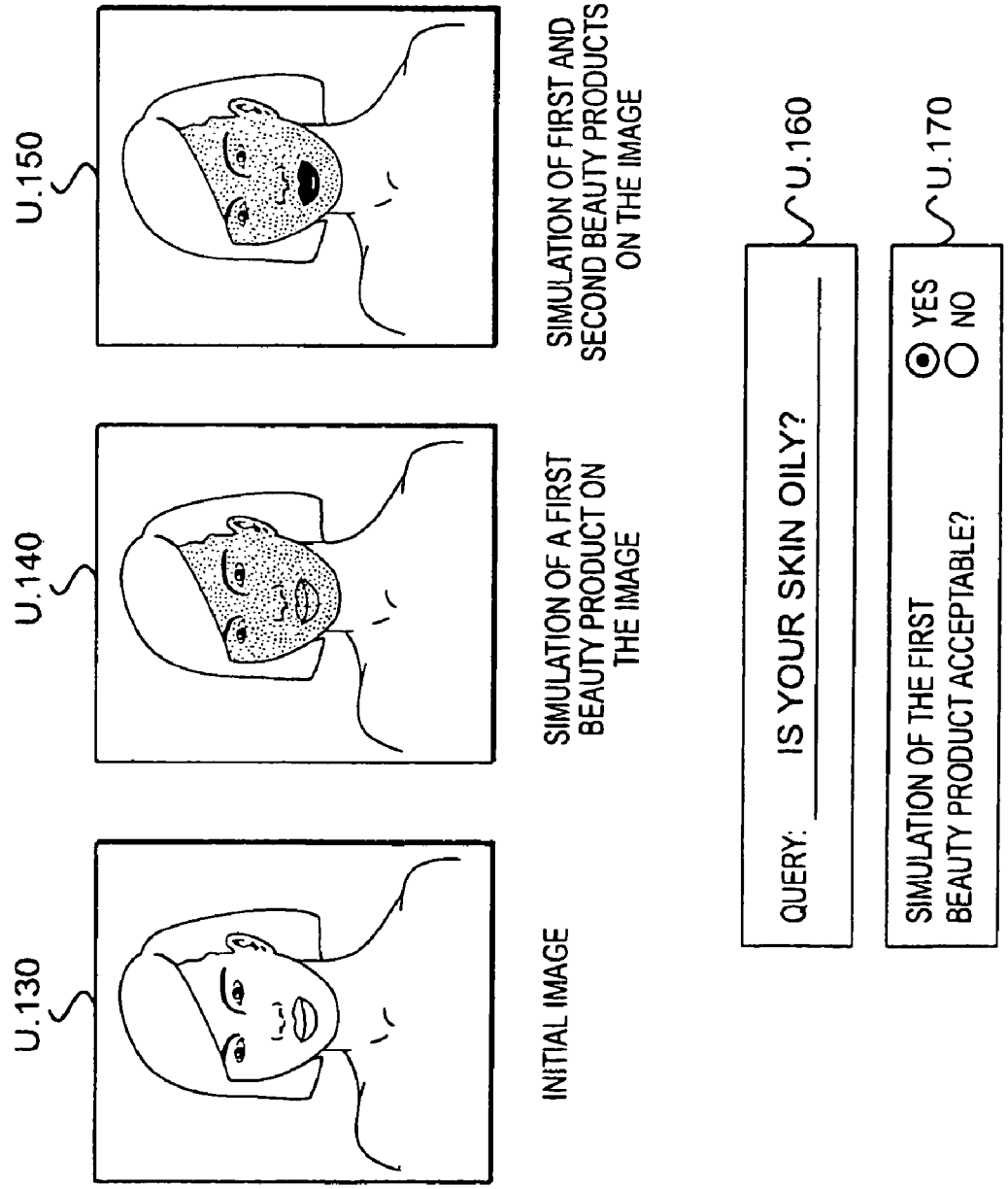
FIG. 22 is an exemplary user interface depicting simulated use of first and second beauty products on a facial image, consistent with the present invention.

As used herein the term "query" refers to a question or prompt in any form that may be presented to a subject to encourage a response from the subject. The query could be presented in any manner enabling the subject to perceive it. For example, the query could be presented in a visual form (e.g., text or image) or audio form. FIG. 22 shows a schematic example of a textual query U.160 associated with a user interface.

In one exemplary embodiment, the query may prompt the subject to input personal information such as physical attributes, lifestyle information, type of look, or personal preferences. Examples of lifestyles might include, but are not limited to: free spirited, adventurous, partier, alternative, and religious. Examples of looks include, but are not limited to, conservative, modern, hot, cool, chic, and retro.

As mentioned above, the method shown in FIG. 21A may include selecting a first beauty product based on the subject's response to the query (S.130). A first beauty product may be automatically selected by analyzing the subject's response using any analytic technique. Such analytic techniques may include, but are not limited to, statistical analysis, modeling, textual analysis, collaborative filtering, artificial intelligence and any other technique that may correlate selection of a first beauty product to a subject's response. Such correlations may be based on populational data or on the experience of experts.

Alternatively, in a method consistent with the invention, the first selected product may be selected from a type of the subject's choosing. For example, if the subject expresses interest in lip stick, analytic techniques may be used to identify a lip stick likely to be compatible with the subject.

The method shown in FIG. 21A may further include enabling a display of a simulation of the first beauty product applied on a facial image (S.140). Image U.140 in FIG. 22 shows an example of a simulation of a first beauty product (e.g., foundation) on a facial image.

Also, as discussed above, the method of FIG. 21A may further include enabling the subject to indicate whether the first beauty product is acceptable (S.150). For example, the subject, after viewing a simulation of the first beauty product might dislike the selection and choose to start over. If the subject wishes to proceed, she may indicate acceptance using, for example, a selectable interface area (U.170) shown in FIG. 22. The interface may include one or more of a displayed button, voice recognition response, or any other mechanism permitting user response. Thus, enabling the subject to indicate acceptance may include providing a selection mechanism to the subject so that the subject may make a selection. This may be accomplished by making accessible to the subject, software for the subject to access via a network or to load onto a personal computer.

If the user indicates that the first product is unacceptable, the method may further include selecting an alternative first beauty product and enabling a display of a simulation of the alternative first beauty product applied on the representative facial image. The alternative first beauty product may be selected using any of the analytic techniques discussed above. Also, the subject may indicate whether the alternative first beauty product is acceptable, as previously discussed.

Once a first product is deemed acceptable to the subject, the method of FIG. 21A may proceed to step S.160 where a second beauty product complementary to the first beauty product may be selected. As used herein, the term "a complementary product" includes one that is either physically, physiologically, biologically, or aesthetically compatible with the subject. Physically compatible may include for example, the fact that a product is unlikely to cause an adverse allergic reaction, and physically blends well with another product. Aesthetic compatibility refers to the fact that two products are aesthetically appealing (or do not clash) when worn together. Information elicited from artificial intelligence, experts and/or populational studies may be stored in a data structure and tapped to identify complementary products. The database may be searched in one of many ways described earlier, including, for example artificial intelligence algorithms.

Selecting the second beauty product may include identifying the second beauty product by using an artificial intelligence engine such as discussed earlier.

Image U.150 in FIG. 22 shows an example of a second beauty product (e.g., lipstick) displayed on a facial image along with a first beauty product (e.g., foundation).

In the method illustrated in FIG. 21A, the simulation of the first beauty product applied on the facial image (e.g., U.140 in FIG. 22) may be replaced on the display device by a new image U.150. Alternatively, as shown in the example of FIG. 22, images U.140 and U.150 may be simultaneously displayed.

Should the second beauty product be unacceptable to the subject, a method consistent with the invention, may include enabling the subject to so indicate and select at least one alternative second complementary beauty product in a manner similar to that described earlier in connection with the first alternative beauty product.

Once a subject is presented with one or more acceptable products, the subject may be provided with purchasing information. Such purchasing information may include, but is not limited to, pricing information, at least one location of a store selling the product, a link to a website selling the product, and/or information enabling a product purchase.

Figure 21B:
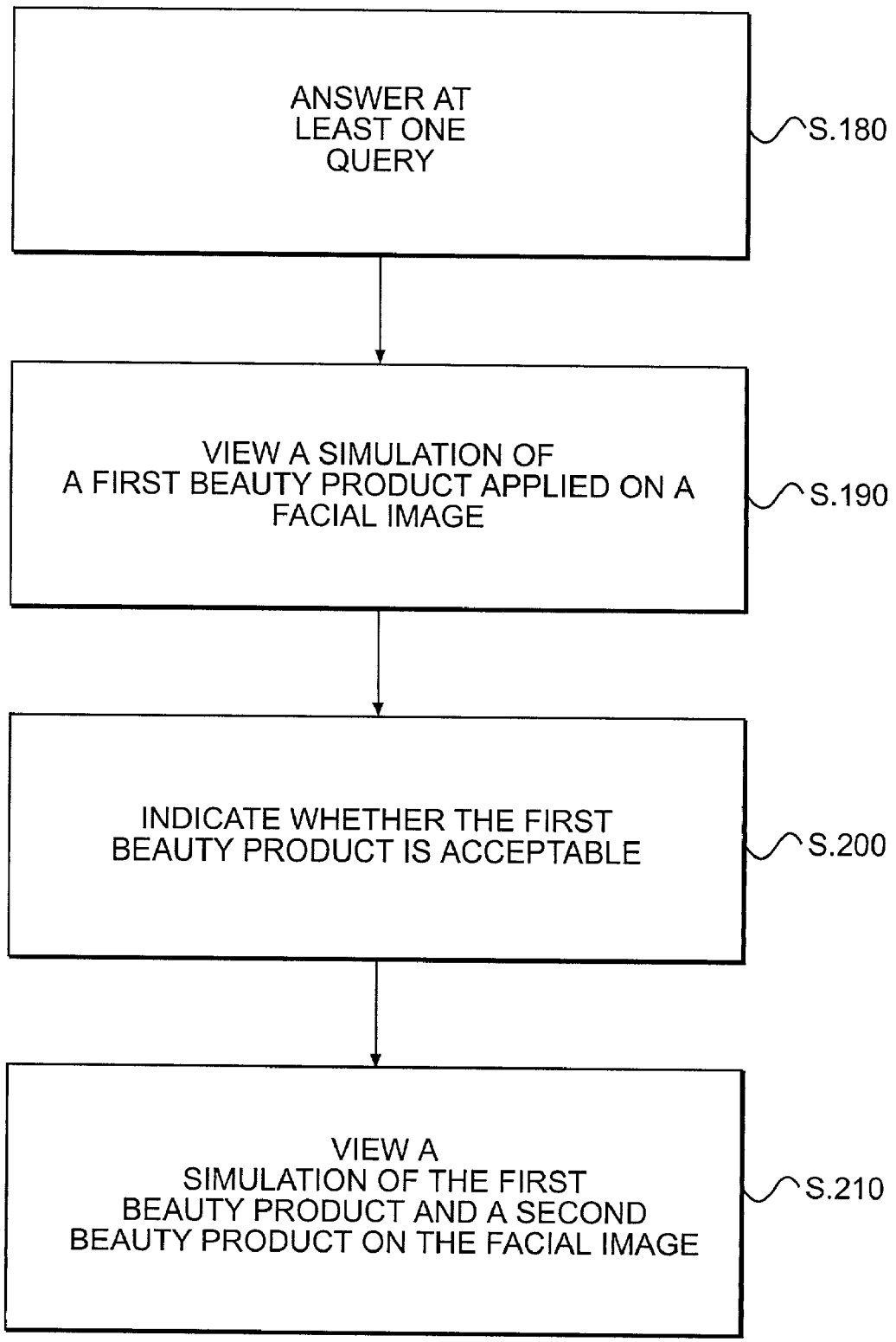
FIG. 21B is a flowchart of an exemplary method for receiving a recommendation for at least one complementary beauty product consistent with the present invention.

FIG. 21B is a flow chart of the method of FIG. 21A, from the subject's perspective. After answering at least one query (S.180), the subject may view on the display device, a simulation of a first beauty product selected based upon the subject's answer to the query (S.190). If the first beauty product is indicated acceptable (S.200), the subject may be presented with a complementary product displayed simultaneously on a facial image containing the first product. (S.210)

Figure 21C:
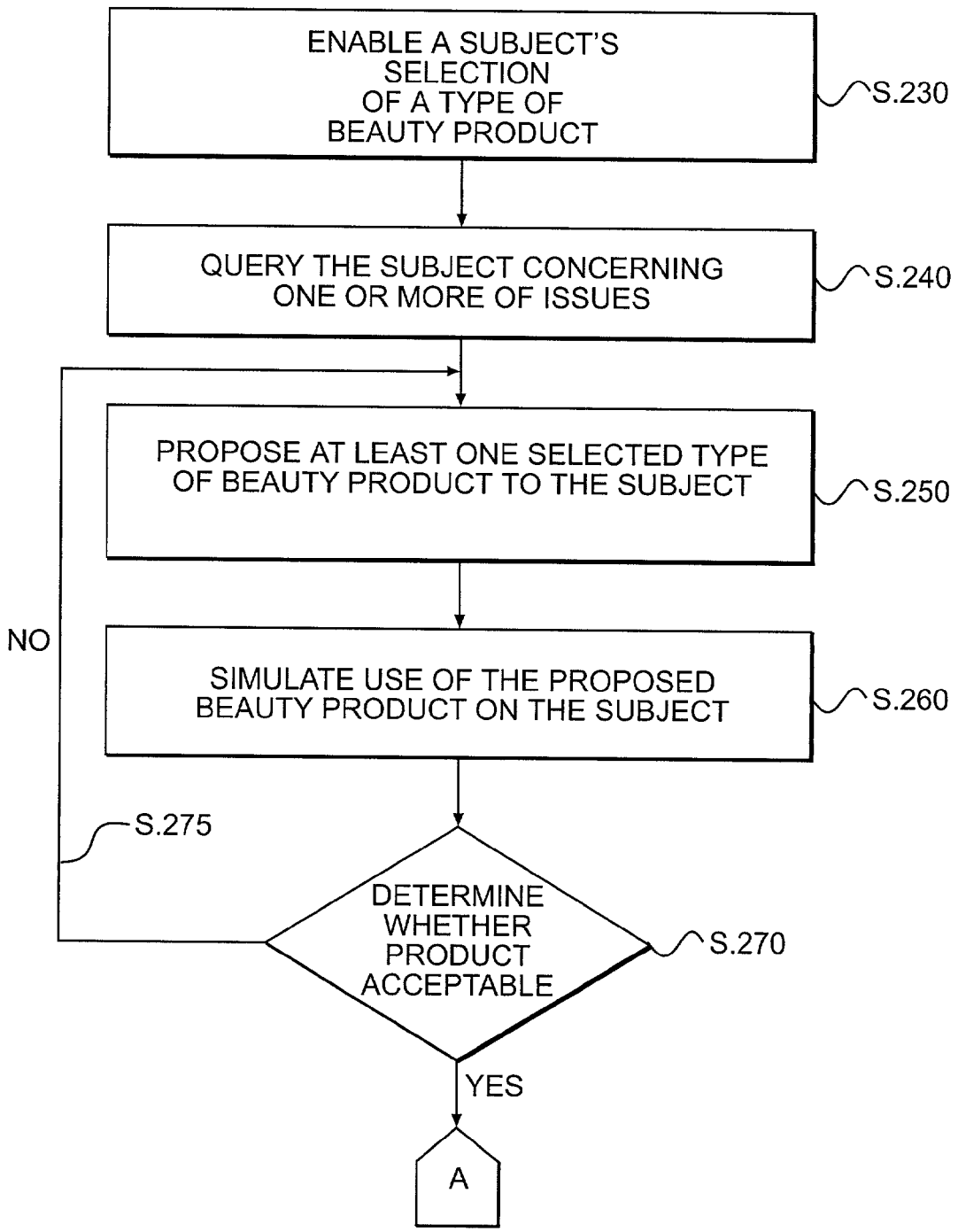
FIGS. 21C and 21D depict a two-page flowchart illustrating an exemplary method for receiving an order for at least one of the proposed products, consistent with the present invention.
Figure 21D:
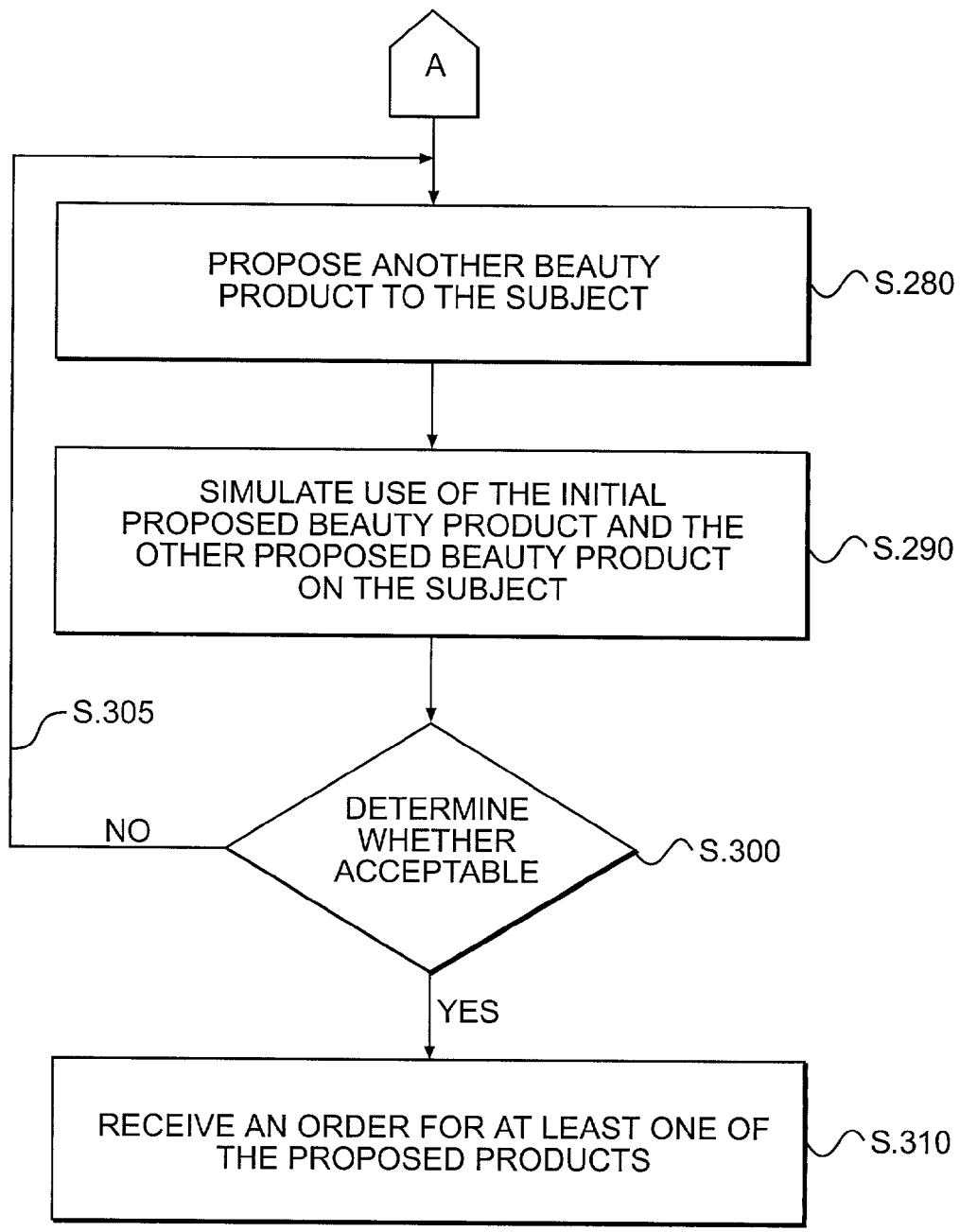

FIGS. 21C and 21D depict a two-page flowchart illustrating an exemplary method for receiving an order for at least one of the proposed products, according to the invention. The method may involve enabling a subject's selection of a category of beauty product (S.230); querying the subject concerning one or more issues (S.240); proposing at least one selected category of beauty product (S.250); simulating use of the proposed beauty product on the subject (S.260); determining whether the product is acceptable (S.270). If the product is acceptable, the method may include proposing another beauty product to the subject (S.280) simulating use of it on the facial image together with the first product (S.290) and if the subject wishes to order, receiving an order from the subject (S.310). If the subject expresses dissatisfaction with either the first selected product at step S.270 or the second proposed product at step S.300, the algorithm may loop (S.275 and S.305, respectively) allowing the subject to view an alternative proposal.

This application may discuss beauty products in connection with use by women. However, it is to be understood that such discussions are for exemplary purposes only. It is to be understood that the invention is equally applicable to all genders, and is not necessarily limited to the beauty industry. It is also to be understood that any functional aspect of the invention can be implemented via any location in the system or network, and data software may be resident at any location either in a network, at a stand-alone site, or on media in the custody and control of a user or subject.

It is to be further understood that the physical mechanisms (e.g. hardware, software, networks, systems) for implementing the methods of the invention are many. Networks, hardware and systems can be configured in a host of ways with software and hardware functionality residing at many alternative locations. In addition, systems other than the exemplary systems disclosed might be used to implement the invention. Therefore, it is to be understood that the methods of the invention are not limited to any particular structure.

Further, methods or portions thereof can be implemented in either an electronic environment, a physical environment, or combinations thereof. Thus, for example, although one or more portions of a method may occur in an electronic environment, a "purchase" portion of the method may occur in a brick and mortar store, or vice versa.

Cross-reference to Concurrently Filed Applications and Global Definitions

This application claims priority on and incorporates by reference the following U.S. Provisional applications: Artificial Intelligence For Use In Cosmetic And Non-Cosmetic Environments, application Ser. No. 60/325,561 (provisional filed Oct. 1, 2001); and Methods And Systems For Cosmetic And Non-Cosmetic Product Selection, application Ser. No. 60/325,559 (provisional filed Oct. 1, 2001).

The following concurrently filed U.S. patent applications are also incorporated herein by reference: Body Image Enhancement, Ser. No. 10/024,480; Methods And Systems For Predicting And/Or Tracking Changes In External Body Conditions, Ser. No. 10/024,354; Methods And Systems For Generating A Prognosis, Ser. No. 10/024,333; Historical Beauty Record, Ser. No. 10/024,622; Identification And Presentation Of Analogous Beauty Case Histories, Ser. No. 10/024,332; Interactive Beauty Analysis, Ser. No. 10/024,481; Feature Extraction In Beauty Analysis, Ser. No. 10/024,495; Simulation Of An Aesthetic Feature On A Facial Image, Ser. No. 10/024,353; Beauty Advisory System And Method, Ser. Nos. 10/024,496; 10/024,620; Virtual Beauty Consultant, Ser. No. 10/024,334 Calibrating Image Capturing, Shop-In-Shop Website Construction, Ser. No. 10/024,352; Early Detection Of Beauty Treatment Progress, Ser. No. 10/024,619; Cosmetic Affinity Indexing, Ser. No. 10/024,356; Systems And Methods For Providing Beauty Guidance, Ser. No. 10/024,621; Methods And Systems Involving Simulated Application Of Beauty Products, Ser. No. 10/024,355; Customized Beauty Tracking Kit, Ser. No. 10/024,351; Analysis Using Three-Dimensional Facial Image, Ser. No. 10/024,615; Body Image Templates With Pre-Applied Beauty Products, Ser. No. 10/024,482; and Image Capture Method, Ser. No. 10/024,482.

To the extent not inconsistent with the invention defined herein, definitions and terminology usage in the above-mentioned concurrently filed applications, the above-mentioned priority applications, and the following global definitions are to be considered in interpreting the language of this patent and the claims herein. Where multiple definitions are provided, they should be considered as a single cumulative definition.

The term "image" may include one or more of two-dimensional and three-dimensional representations. In certain examples consistent with the invention, a plurality of images from different perspectives may be used to construct a three-dimensional image. In a broader sense, only a single image may be used. Depending on the embodiment, the term "image" may include either a visually perceptible image or electronic image data that may be either used to construct a visually perceptible image or to derive information about the subject. The image may be a body image corresponding to an anatomical portion of the subject, and may represent, for example, the subject's entire face, or a portion of the subject's face. The image may be a detailed picture (e.g., a digital image or a photograph) of a portion of the subject's body and/or a topological plot mapping contours of a portion of subject's body. If the image is representative of an external body condition, the image could be either an actual image showing the condition or an image including symbolizations of the condition, for example. The image may be an actual or a simulated image. Simulated images may include wholly or partially generated computer images, images based on existing images, and images based on stored features of a subject.

The term "image capture device", similar terms, and terms representing structures with similar functions may include one or more of a digital camera, webcam, film camera, analog camera, digital video camera, scanner, facsimile machine, copy machine, infrared imager, ultra-sound imaging device, or any other mechanism for acquiring an image of a subject's external body condition, an image of the subject's countenance, an/or an image of the subject's skin. An ultrasonic device might provide skin thickness information, or it might create a map on an area of the external location. Thus, the term "image" as used herein may be broader than a picture. Combinations of image capture devices may be used. For example, an image captured on photographic paper using a film camera might then be scanned on a flat bed scanner to create another image.

The term "capturing (an image)", or any form thereof, refers to the use of an image capture device to acquire an image. "Capturing" may refer to the direct act of using the image capture device to acquire the image. It may also include indirect acts to promote acquisition. To this end, "capturing" may include the indirect acts of providing access to hardware, or to at least one of a client-based algorithm and a server-based algorithm for causing the image capture device to capture an image. This may be accomplished by providing a user with software to aid in the image capture process, or providing the user with access to a network location at which the software resides. Also consistent with certain embodiments of the invention, capturing may include at least one of receiving an instruction from the subject to capture an image, indicating to the subject before the image is captured, and indicating to the subject when the image is captured.

The term "image processing technique" or similar terms, may include a software program, computer, application specific integrated circuit, electronic device and/or a processor designed to identify in an image one or more characteristics, such as a skin condition. Such techniques may involve binarization, image partitioning, Fourier transforms, fast Fourier transforms (FFTs), and/or discrete cosine transforms may be performed on all or part of the image, resulting in coefficients. Based on the coefficients, conditions may be located, as known in the art. Artificial intelligence, such as fuzzy logic, neural networks, genetic programming and decision tree programming, may also be used to identify conditions. Alternatively, one or more digital filters may be passed through the image for locating specific conditions. These examples are provided for illustrative purposes with the understanding that any image processing technique may be used.

The term "network interface" or similar terms, refer to any mechanism for aiding communications between various nodes or locations in a network. A network interface may include, for example a bus, a modem, or any other input/output structure. A network interface may permit a connection to any network capable of being connected to an input and/or output module located within at least one or more of the following exemplary networks: an Ethernet network, an Internet Protocol network, a telephone network, a radio network, a cellular network, or any mechanism for permitting communication between two or more modes or remote locations. In some invention embodiments, a network interface might also include a user interface.

The term "user interface" may include at least one component such as a keyboard, key pad, mouse, track ball, telephone, scanner, microphone, touch screen, web cam, interactive voice response system (IVR), voice recognition system or any other suitable input mechanism for conveying information. A user interface may also include an input port connected by a wired, optical, or wireless connection for electromagnetic transmissions. In some embodiments, a user interface may include connections to other computer systems to receive the input commands and data therefrom. User interface may further include a data reading device such as a disk drive for receiving input data from and writing data to storage media such as magnetic and optical disks.

As used herein terms such as "external body condition", "skin condition", and "actual condition" refer to conditions of at least one of the skin, teeth, hair, eyebrows, eyelashes, body hair, facial hair, fingernails, and/or toenails, or any other externality. Examples of skin conditions may include elasticity, dryness, cellulitis, sweating, aging, wrinkles, melanoma, exfoliation, desquamation, homogeneity of color, creases, liver spots, clarity, lines, micro-circulation, shininess, softness, smoothness, tone, texture, matitty, hydration, sag, suppleness, stress, springiness, firmness, sebum production, cleanliness, translucency, luminosity, irritation, redness, vasocolation, vasomotion, vasodilation, vasoconstriction, pigmentation, freckles, blemishes, oiliness, pore distribution, pore size, moles, birthmarks, acne, blackheads, whiteheads, pockmarks, warts, pustules, boils, blisters, marks, smudges, specks, psoriasis and other characteristics associated with the subject's skin. Examples of hair conditions may include keratin plug, length, dryness, oiliness, dandruff, pigmentation, thickness, density, root conditions, split ends, hair loss, hair thinning, scales, staging, cleanliness and other properties related to the subject's hair. Examples of fingernail and toenail conditions may include onychomycosis, split nails, delaminating, psoriasis, brilliancy, lines, spots, coloration, gloss, strength, brittleness, thickness, hangnail, length, disease, and other characteristics related to the subject's nails. Other conditions may include, for example, size and proportion of facial features, teeth discoloration, and any other aesthetic-related or physical, physiological, or biological conditions of the user.

"Enabling", "facilitating", and "causing" an action refer to one or more of a direct act of performing the action, and any indirect act of encouraging or being an accessory to the action. Thus, the terms include partnering or cooperating with an entity who performs the action and/or referring commerce to or having commerce referred from an entity who performs the action. Other examples of indirect activity encompassed within the definitions of "enabling", "facilitating", and "causing" may include providing a subject with one or more of tools to knowingly aid in performing the action, providing instructions on how to perform the action, providing prompts or cues to perform the action, or expressly encouraging performance of the action. Indirect activity may also include cooperating with an entity who either directly performs the action or who helps another perform the action. Tools may include software, hardware, or access (either directly, through hyperlink, or some other type of cooperation or partnering) to a network location (e.g., web site) providing tools to aid in performing the action. Thus, phrases such as "enabling access" and "enabling display" do not necessary require that the actor actually access or display anything. For example, the actor may perform the enabling function by affiliating with an entity who performs the action, or by providing instructions, tools, or encouragement for another to do the accessing and displaying.

Forms of the word "displaying" and like terms may also include indirect acts such as providing content for transmission over a network to a display device, regardless of whether the display device is in the custody or control of the sender. Any entity in a chain of delivering information for display performs an act of "displaying", as the term is used herein.

Likewise, the term "providing" includes direct and indirect activities. For example, providing access to a computer program may include at least one of providing access over a network to the computer program, and creating or distributing to the subject a computer program configured to run on the subject's workstation or computer. For example, a first party may direct network traffic to (either through electronic links or through encouragement to visit) a server or web site run by a second party. If the second party maintains a particular piece of software thereon, then it is to be understood that within the meaning of "providing access" as used herein, the first party is said to provide access to the particular software. Or if the first party directs a subject to a second party who in turn ships the particular software to the user, the first party is said to provide the user with access to the particular software. (Of course, in both of the above instances, the second party would also be providing access within the meaning of the phrase as used herein.) "Receiving" may include at least one of acquisition via a network, via verbally communication, via electronic transmission, via telephone transmission, in hard-copy form, or through any other mechanism enabling reception. In addition, "receiving" may occur either directly or indirectly. For example, receipt may occur through a third party acting on another party's behalf, as an agent of another, or in concert with another. Regardless, all such indirect and direct actions are intended to be covered by the term "receiving" as used herein. A received request, for example, may take one of many forms. It may simply be a checked box, clicked button, submitted form or oral affirmation. Or it might be a typed or handwritten textual request. Receiving may occur through an on-line interest form, e-mail, facsimile, telephone, interactive voice response system, or file transfer protocol transmitted electronically over a network at a web site, an internet protocol address, or a network account. A request may be received from a subject for whom information is sought, or an entity acting on the subject's behalf. "Receiving" may involve receipt directly or indirectly through one or more networks and/or storage mediums. Receipt may occur physically such as in hard copy form, via mail delivery or other courier delivery.

Forms of the word "maintain" are used broadly to include gathering, storing, accessing, providing access to, or making something available for access, either directly or indirectly. For example, those who maintain information include entities who provide a link to a site of a third party where the information is stored.

Consistent with the concepts set forth above, all other recited actions such as, for example, obtaining, determining, generating, selecting, applying, simulating, presenting, etc, are inclusive of direct and indirect actions. Thus, for purposes of interpreting the following claims, an entity performs a recited action through either direct or indirect activity. Further examples of indirect activity include sending signals, providing software, providing instructions, cooperating with an entity to have the entity perform the action, outsourcing direct or indirect actions, or serving in any way as an accessory to the specified action.

The term "product" is used to generically refer to tangible merchandise, goods, services, and actions performed. A "beauty product," "beauty care product," "cosmetic product" or similar terms, refer to products (as defined above) for effecting one or more external body conditions, such as conditions of the skin, hair and nails. Examples of tangible merchandise forms of beauty products include cosmetic goods, such as treatment products, personal cleansing products, and makeup products, in any form (e.g., ointments, creams, gels, sprays, supplement, ingesta, inhalants, lotions, cakes, liquids, and powders.)

Examples of service forms of beauty products include hair styling, hair cutting, hair coloring, hair removal, skin treatment, make-up application, and any other offering for aesthetic enhancement. Examples of other actions performed include massages, facial rubs, deep cleansings, applications of beauty product, exercise, therapy, or any other action effecting the external body condition whether performed by a professional, the subject, or an acquaintance of the subject.

The following is exemplary and non-exhaustive listing of a few beauty products—scrubs, rinses, washes, moisturizers, wrinkle removers, exfoliates, toners, cleansers, conditioners, shampoos, cuticle creams, oils, and anti-fungal substances, anti-aging products, anti-wrinkle products, anti-freckle products, skin conditioners, skin toners, skin coloring agents, tanners, bronzers, skin lighteners, hair coloring, hair cleansing, hair styling, elasticity enhancing products, agents, blushes, mascaras, eyeliners, lip liners, lipsticks, lip glosses, eyebrow liners, eye shadows, nail polishes, foundations, concealers, dental whitening products, cellulite reduction products, hair straighteners and curlers, and weight reduction products. A beauty care treatment regimen may involve the administration of one or more products, as defined above.

The terms "beauty advice", "beauty guidance", and similar terms are used interchangeably to refer to the provision of beauty related information to a subject. Advice or guidance includes one or more of beauty product recommendations (e.g., cosmetic product recommendations for products to treat conditions the subject is prompted to evaluate), remedial measures, preventative measures, predictions, prognoses, price and availability information, application and use information, suggestions for complementary products, lifestyle or dietary recommendations, or any other information intended to aid a subject in a course of future conduct, to aid a subject in understanding past occurrences, to reflect information about some future occurrences related to the subject's beauty or to aid a subject in understanding beauty products, as defined above.

The term "network" may include a public network such as the Internet or a telephony network, a private network, a virtual private network, or any other mechanism for enabling communication between two or more nodes or locations. The network may include one or more of wired and wireless connections. Wireless communications may include radio transmission via the airwaves, however, those of ordinary skill in the art will appreciate that various other communication techniques can be used to provide wireless transmission including infrared line of sight, cellular, microwave, satellite, blue-tooth packet radio and spread spectrum radio. Wireless data may include, but is not limited to, paging, text messaging, e-mail, Internet access and other specialized data applications specifically excluding or including voice transmission.

In some instances consistent with the invention, a network may include a courier network (e.g. postal service, United Parcel Service, Federal Express, etc.). Other types of networks that are to be considered within the scope of the invention include local area networks, metropolitan area networks, wide area networks, ad hoc networks, or any mechanism for facilitating communication between two nodes or remote locations.

"Artificial intelligence" (AI) is used herein to broadly describe any computationally intelligent systems that combine knowledge, techniques, and methodologies. An AI engine may be any system configured to apply knowledge and that can adapt itself and learn to do better in changing environments. Thus, the AI engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, or soft computing. Employing any computationally intelligent techniques, the AI engine may learn to adapt to unknown or changing environment for better performance. AI engines may be implemented or provided with a wide variety of components or systems, including one or more of the following: central processing units, co-processors, memories, registers, or other data processing devices and subsystems.

AI engines may be trained based on input such as product information, expert advice, user profile, or data based on sensory perceptions. Using input an AI engine may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, or recording learning. As a result of the training, AI engine may learn to modify its behavior in response to its environment, and obtain knowledge. Knowledge may represent any information upon which AI engine may determine an appropriate response to new data or situations. Knowledge may represent, for example, relationship information between two or more products. Knowledge may be stored in any form at any convenient location, such as a database.

Since AI engine may learn to modify its behavior, information describing relationships for a universe of all combinations of products may not need to be maintained by the AI engine or any other component of the system.

"Personal information", "subject specific information", "user specific information", "user Profile", "personal characteristics", "personal attributes", "profile information", and like terms (collectively referred to in this section as "personal information") may broadly encompass any information about the subject or user. Such information may, for example, fall within categories such as physical characteristics, fashion preferences, demographics, nutritional information, cosmetic usage information, medical history information, environmental information, beauty product usage information, lifestyle, and may include information such as name; age; birth date; height; weight; ethnicity; eating habits; vacation patterns; geographic location of the individual's residence, location, or work; work habits; sleep habits; toiletries used; exercise habits; relaxation habits; beauty care habits; smoking and drinking habits; sun exposure habits; use of sunscreen; propensity to tan; number of sunburns and serious sunburns; dietary restrictions; dietary supplements or vitamins used; diagnosed conditions affecting the external body, such as melanoma; an image, such as a picture or a multimedia file of the subject; facial feature characteristics; family history information such as physical characteristics information about relatives of the subject (e.g., premature balding, graying, wrinkles, etc.); external body condition (as defined previously); color preferences, clothing style preferences, travel habits; entertainment preferences; fitness information; adverse reactions to products, compounds, or elements (e.g., sun exposure); body chemistry, use of prior beauty care products and their effectiveness; purchasing, shopping, and browsing habits; hobbies; marital status; whether the subject is a parent; country of residence; region of residence; birth country and region; religious affiliation; political affiliation; whether the subject is an urban dweller, suburban dweller or rural area dweller; size of urban area in which the subject lives; whether the subject is retired; annual income, sexual preference, or any other information reflecting habits, preferences, or affiliations of the subject.

Personal information may also include information electronically gleaned by tracking the subject's electronic browsing or purchasing habits, or as the result of cookies maintained on the subject's computer, responses to surveys, or any other mechanism providing information related to the subject. In addition, personal information may be gathered through non-electronic mechanisms such as hard copy surveys, personal interviews, or consumer preference polls.

"Complementary" and "complementary product" refers to one or more of physical, physiological, biologically, and aesthetic compatibility. A product may be complementary with one or more of another product, a group of products, or a subject. In that latter instance, whether a product is considered "complementary" may be a function of personal information of the subject. Thus, for example a product may be complementary if it is unlikely to cause an adverse allergic reaction; if it physically blends well with another product; or if it is aesthetically consistent with the subject or one or more other products. Aesthetic compatibly may refer to the fact that two products are aesthetically appealing (or do not clash) when worn together. The identification of a complementary product may also be based on product characteristics, user preferences, survey data, or expert advice.

As used herein, the words "may" and "may be" are to be interpreted in an open-ended, non-restrictive manner. At minimum, "may" and "may be" are to be interpreted as definitively including structure or acts recited. Further, the word "or" is to be interpreted in the conjunctive and the disjunctive.

While flow charts presented herein illustrate a series of sequential blocks for exemplary purposes, the order of blocks is not critical to the invention in its broadest sense. Further, blocks may be omitted and others added without departing from the spirit of the invention. Also, the invention may include combinations of features described in connection with differing embodiments.

Although a focus of the disclosure may be on server-side methods, it is nevertheless to be understood that the invention includes corresponding client-side methods, software, articles of manufacture, and computer readable media, and that computer readable media can be used to store instructions for some or all of the methods described herein. Further, it is to be understood that disclosed structures define means for implementing the functionality described herein, and that the invention includes such means for performing the disclosed functions.

In the foregoing Description of Exemplary Embodiments, various features are grouped together in a single embodiment for purposes of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Description of the Exemplary Embodiments, with each claim standing on its own as a separate embodiment of the invention.

What is claimed is:

1. A method of providing beauty advice, the method comprising:
   receiving user-specific information;
   accessing a data structure containing information reflecting relationships between categories of user-specific information and beauty advice, the information reflecting relationships derived from at least one of consumer preferences and expert advice, wherein the data structure includes information characterizing a plurality of beauty products and information about suitability of combining at least some of the plurality of beauty products with other of the plurality of beauty products;
   comparing, using an artificial intelligence engine, the received user-specific information with the accessed data;
   identifying, using the artificial intelligence engine, beauty advice determined by the artificial intelligence engine to be related to the user-specific information; and
   providing the identified beauty advice to the user.

2. The method of claim 1, wherein the user-specific information includes personal information of at least one of skin type, skin tone, hair style, hair color, cosmetic color and product preferences, allergy information, demographic information, climate information, lifestyle information, fashion preferences, prior purchases, prior expressed interest, and prior browsing patterns.

3. The method of claims 1 or 2, wherein the user-specific information includes an identification of at least one user-specified product.

4. The method of claim 1, wherein the artificial intelligence engine is based on at least one of a neural network, constraint program, fuzzy logic, classification, conventional artificial intelligence, symbolic manipulation, fuzzy set theory, evolutionary computation, cybernetics, data mining, approximate reasoning, derivative-free optimization, and soft computing.

5. The method of claim 1 conducted, at least in part, in a network environment, wherein receiving user-specific information occurs via a network and in at least one location remote from the user, and wherein providing occurs via the network.

6. The method of claim 1, wherein the data reflecting relationships is data about at least one of consumer preferences and expert advice.

7. The method of claim 3, wherein the beauty advice includes a product recommendation, wherein during comparing the artificial intelligence engine processes information relating to the at least one user-specified product, wherein during identifying the artificial intelligence engine identifies at least one product complementary to the at least one user-specified product, and wherein during providing, the user is advised of the at least one identified complementary product.

8. The method of claim 7, wherein both the at least one user-specified product and the at least one identified complementary product are cosmetic products.

9. The method of claim 7, wherein only one of the user-specified product and the identified complementary product is a cosmetic product.

10. The method of claim 7, wherein the user-specified product is a cosmetic product and the identified complementary product is at least one of an apparel product and an accessory product.

11. The method of claim 7, wherein the identified complementary product is a cosmetic product and the user-specified product is at least one of an apparel product and an accessory product.

12. The method of claim 3, wherein the user-specified product is at least two products, and wherein during identifying, the artificial intelligence engine identifies at least one product complementary to a combination of the at least two user-selected products.

13. The method of claim 1, wherein the information reflecting relationships is derived by surveying at least one of consumer preferences and consumer habits.

14. The method of claim 7, further comprising offering the user an opportunity to purchase the at least one user-specified product and the at least one complementary product.

15. The method of claim 7, wherein the at least one user-specified product has an associated aesthetic characteristic, and wherein the artificial intelligence engine is configured to identify at least one product with an aesthetic characteristic complementary to the aesthetic characteristic of the user-specified product.

16. The method of claim 7, further comprising providing the user with an option to indicate an interest in purchasing the at least one user-specified product, and wherein notifying the user of the at least one complementary product occurs before the user completes a purchase of the at least one user-specified product.

17. The method of claim 1, wherein information characterizing a plurality of beauty products includes information about cosmetic color.

18. The method of claim 1, wherein information characterizing a plurality of beauty products includes information about inter-beauty product compatibility.

19. The method of claim 1, wherein receiving user-specific information includes receiving from the user a selection of a combination of at least two of the plurality of beauty products, wherein suitability of combining information is maintained on less than a universe of all combinations of the plurality of beauty products, and wherein when an individual selects a combination of beauty products for which suitability of combining information is not directly maintained, the artificial intelligence engine, during identifying, identifies a product likely to be complementary to the user-selected combination.

20. A method of identifying a combination of complementary beauty products, the method comprising:
   maintaining information characterizing a plurality of beauty products;
   maintaining information about suitability of use of at least some of the plurality of beauty products with other of the plurality of beauty products;
   receiving from a user a selection of at least two of the plurality of beauty products;

processing, using an artificial intelligence engine, information characterizing the at least two selected beauty products and suitability of use information to thereby identify at least one additional product, complementary to a combination of the at least two selected products; and notifying the user of the at least one additional product.

21. The method of claim 20, further comprising maintaining personal information about the user, and wherein during processing, the artificial intelligence engine uses at least some of the personal information, information characterizing the at least two of the plurality of beauty products selected by the user, and at least some of the maintained suitability of use information.

22. The method of claim 20 conducted, at least in part, in a network environment, wherein receiving the user selection occurs via a network and in at least one location remote from the user, and wherein notifying occurs via the network.

23. A method of identifying complementary products, the method comprising:

receiving from a user a selection of at least one user-specified product;

accessing through an artificial intelligence search engine characterizations of a plurality of products;

accessing through the artificial intelligence search engine information about relationships between at least some of the plurality of products;

identifying, by the artificial intelligence engine, at least one recommended product complementary to the at least one user-specified product using at least the information about product relationships; and notifying the user of the at least one recommended complementary product.

24. The method of claim 23 conducted, at least in part, in a network environment, wherein receiving the user selection occurs via a network in at least one location remote from the user, and wherein notifying occurs via the network.

25. The method of claim 23, wherein both the at least one user-specified product and the at least one recommended complementary product are cosmetic products.

26. The method of claim 23, wherein only one of the user-specified product and the at least one recommended complementary product is a cosmetic product.

27. The method of claim 23, wherein the at least one user-specified product is a cosmetic product and the at least one recommended complementary product is at least one of an apparel product and an accessory product.

28. The method of claim 23, wherein the at least one recommended complementary product is a cosmetic product and the user-specified product is at least one of an apparel product and an accessory product.

29. The method of claim 23, wherein the user-specified product is at least two products, and wherein during identifying, the artificial intelligence engine identifies at least one product complementary to a combination of the at least two user-specified products.

30. The method of claim 23, wherein the information about relationships is obtained by surveying at least one of consumer preferences and consumer habits.

31. The method of claim 23, further comprising offering the user an opportunity to purchase the at least one user-specified product and the at least one recommended complementary product.

32. The method of claim 23, wherein the at least one user-specified product has an associated aesthetic characteristic, and wherein the artificial intelligence engine is configured to identify at least one product with an aesthetic characteristic complementary to the aesthetic characteristic of the user-specified product.

33. The method of claim 23, further comprising providing the user with an option to indicate an interest in purchasing the at least one user-specified product, and wherein notifying the user of the at least one recommended complementary product occurs before the user completes a purchase of the at least one user-specified product.

34. The method of claim 33, wherein the characterizations of a plurality of products include characterizations of a plurality of cosmetic and non-cosmetic products, and wherein the information about relationships includes information about relationships between at least some of the plurality of cosmetic and non-cosmetic products.

35. A system for providing beauty advice, the system comprising:

a data structure containing information reflecting relationships between categories of user-specific information and beauty advice, the information reflecting relationships derived from at least one of consumer preferences and expert advice, wherein the data structure includes information characterizing a plurality of beauty products and information about suitability of combining at least some of the plurality of beauty products with other of the plurality of beauty products;

an artificial intelligence engine, configured to receive and process the information reflecting relationships and user-specific information, to thereby identify beauty advice determined by the artificial intelligence engine to be related to the user-specific information; and an interface for conveying the identified beauty advice to the user.

36. The system of claim 35, wherein the user-specific information includes personal information of at least one of skin type, skin tone, hair style, hair color, cosmetic color and product preferences, allergy information, demographic information, climate information, lifestyle information, fashion preferences, prior purchases, prior expressed interest, and prior browsing patterns.

37. The system of claims 35 or 36, wherein the user-specific information includes an identification of at least one user-specified product.

38. The system of claim 35, wherein the artificial intelligence engine is based on at least one of a neural network, constraint program, fuzzy logic, classification, conventional artificial intelligence, symbolic manipulation, fuzzy set theory, evolutionary computation, cybernetics, data mining, approximate reasoning, derivative-free optimization, and soft computing.

39. The system of claim 35, wherein the interface is a network interface configured to receive user-specific information via a network and in at least one location remote from the user, and to transmit the beauty advice to a user located remote from the artificial intelligence engine.

40. The system of claim 35, wherein the information reflecting relationships includes data about at least one of consumer preferences and expert advice.

41. The system of claim 35, wherein the beauty advice includes a product recommendation, wherein the user-specific information includes at least one user-specified product, wherein during identifying the artificial intelligence engine identifies at least one product complementary to the at least one user-specified product, and wherein during conveying, the user is advised of the at least one complementary product.

42. The system of claim 41, wherein both the at least one user-specified product and the at least one identified complementary product are cosmetic products.

43. The system of claim 41, wherein only one of the at least one user-specified product and the at least one identified complementary product is a cosmetic product.

44. The system of claim 41, wherein the at least one user-specified product is a cosmetic product and the at least one identified complementary product is at least one of an apparel product and an accessory product.

45. The system of claim 41, wherein the at least one identified complementary product is a cosmetic product and the at least one user-specified product is at least one of an apparel product and an accessory product.

46. The system of claim 41, wherein the at least one user-specified product is at least two products, and wherein during identifying, the artificial intelligence engine identifies at least one product complementary to a combination of the at least two user-selected products.

47. The system of claim 35, wherein the information reflecting relationships is derived by surveying at least one of consumer preferences and consumer habits.

48. The system of claim 41, further comprising a purchase engine for offering the user an opportunity to purchase the at least one user-specified product and the at least one complementary product.

49. The method of claim 41, further comprising a purchase engine for providing the user with an option to indicate an interest in purchasing the at least one user-specified product, and wherein the purchase engine notifies the user of the at least one complementary product before the user completes a purchase of the at least one user-specified product.

50. The system of claim 41, wherein the at least one user-specified product has an associated aesthetic characteristic, and wherein the artificial intelligence engine is configured to identify at least one product with an aesthetic characteristic complementary to the aesthetic characteristic of the user-specified product.

51. The system of claim 35, wherein information characterizing a plurality of beauty products includes information about cosmetic color.

52. The system of claim 35, wherein information characterizing a plurality of beauty products includes information about inter-beauty product compatibility.

53. The system of claim 35, wherein the user-specific information includes a user selection of a combination of at least two of the plurality of beauty products, wherein information about relationships is information on less than a universe of all combinations of the plurality of beauty products, and wherein when an individual selects a combination of beauty products for which suitability of combining information is directly not maintained, the artificial intelligence engine is configured to identify a product likely to be complementary to the user-selected combination.

54. A system for identifying a product complementary to a selected product, the system comprising:
  an interface for receiving from a user a selection of at least one of a plurality of products;
  at least one location for storing information characterizing the plurality of products;
  at least one location for storing information about suitability of using at least one of the plurality of products with at least one other of the plurality of products;
  at least one location for storing personal information about a user; and
  an artificial intelligence engine configured to process information reflective of the at least one user-selected product, at least some of the characterizing information, at least some of the suitability information, and at least some of the personal information, and to identify therefrom at least one product complementary to the at least one user-selected product.

55. The system of claim 54, wherein the artificial intelligence engine is based on at least one of a neural network, constraint program, fuzzy logic, classification, conventional artificial intelligence, symbolic manipulation, fuzzy set theory, evolutionary computation, cybernetics, data mining, approximate reasoning, derivative-free optimization, and soft computing.

56. The system of claim 54, wherein the interface is configured to receive from the user a selection of at least two products, and wherein the artificial intelligence engine is configured to identify at least one product complementary to the at least two selected products.

57. The system of claim 54, wherein the information about suitability of using is based on a survey of consumers.

58. The system of claim 54, wherein the information about suitability of using is based on expert advice.

59. The system of claim 54, further comprising a purchase engine for offering the user an opportunity to purchase the at least one selected product and the at least one complementary product.

60. The system of claim 54, wherein the at least one product selected by the user has an associated aesthetic characteristic, and wherein the artificial intelligence engine is configured to identify at least one product with an aesthetic characteristic complementary to the aesthetic characteristic of the at least one selected product.

61. The system of claim 54, wherein the at least one product selected by the user and the at least one complementary product are each chosen from at least one of cosmetics, apparel, and accessories.

62. The system of claim 54, wherein the user interface is configured to receive from the user an indication of interest in purchasing the at least one product, and as a conduit for notifying the user of the complementary product before the user completes a purchase of the at least one selected product.

63. The system of claim 54, wherein the user selection of at least one product is a cosmetic, and wherein the at least one complementary product is a cosmetic product that aesthetically and physically complements the at least one selected product.

64. The system of claim 54, wherein the user selection of at least one product is a beauty product chosen from at least one of tangible merchandise, services, diagnostics, beauty regimen, and advice.

65. The system of claim 54, wherein personal information includes information relating to at least one of prior product selection, physical characteristics, and a user preference.

66. The system of claim 54, wherein the personal information includes a prior product selection by the user, wherein the artificial intelligence engine is configured to process the prior product selection, and wherein during providing, a product recommendation is presented to the user.

67. A method of identifying complementary products, the method comprising:
  receiving subject-specific information;
  using the subject-specific information to identify a first product;
  accessing through an artificial intelligence search engine characterizations of a plurality of products;
  accessing through the artificial intelligence search engine information about relationships between at least some of the plurality of products;

identifying, by the artificial intelligence engine, a second recommended product complementary to the first product based on at least the information about relationships; and notifying the user of the second recommended complementary product.

68. A method of recommending at least one complementary beauty product, the method comprising:

causing at least one query to be presented to a subject;

selecting a first beauty product based on the subject's response to the query;

enabling a display of a simulation of the first beauty product applied on a facial image;

enabling the subject to indicate whether the first beauty product is acceptable, wherein when the first product is indicated as being acceptable, the method further comprises selecting at least one second beauty product complementary to the first beauty product based on information reflecting a relationship between the first beauty product and the second beauty product; and enabling a display of a simulation of the first and second beauty products applied on the facial image.

69. The method of claim 68, wherein the first beauty product is chosen from a category of beauty products pre-selected by the subject.

70. The method of claim 69, wherein the category of beauty products is at least one of mascaras, eye shadows, eye liners, foundations, concealers, blushes, lip sticks, lip glosses, liners, hair treatments, and hair colorings.

71. The method of claim 68, wherein the query prompts the subject to select at least one of a type of lifestyle and a type of look.

72. The method of claim 68, wherein when the first product is indicated as being unacceptable, the method further comprises selecting an alternative first beauty product and enabling a display of a simulation of the alternative first beauty product applied on the facial image.

73. The method of claim 72, further comprising selecting at least one alternative second beauty product complementary to the alternative first beauty product and enabling a display of a simulation of the alternative first and the alternative second beauty products applied on the facial image.

74. The method of claim 72, further comprising enabling the subject to indicate whether the alternative first beauty product is acceptable.

75. The method of claim 68, wherein enabling the subject to indicate whether the first beauty product is acceptable includes prompting the subject to indicate whether the subject believes the first beauty product has an acceptable appearance.

76. The method of claim 68, wherein the first and second beauty products are complementary by virtue of at least one of aesthetic quality and brand name.

77. The method of claim 68, wherein the simulation of the first beauty product applied on the facial image is replaced on a display by a simulation of the first and second beauty products applied on the facial image.

78. The method of claim 68, wherein the simulation of the first beauty product applied on the facial image is displayed adjacent a display of the simulation of the first and second beauty products applied on the facial image.

79. The method of claim 68, further comprising enabling the subject to indicate whether the second beauty product is acceptable, wherein when the second product is indicated as being unacceptable, the method further comprises selecting at least one alternative second beauty product complementary with the first beauty product and enabling a display of a simulation of the first beauty product and the alternative second beauty product applied on the facial image.

80. The method of claim 68, further comprising enabling the subject to receive information informing the subject about purchasing at least one of the first beauty product and the second beauty product.

81. The method of claim 68, wherein the facial image is a facial image of the subject.

82. The method of claim 68, further comprising enabling the subject to alter the facial image based on a self-evaluation of the subject's face.

83. The method of claim 68, wherein selecting the second beauty product further comprises identifying the second beauty product using an artificial intelligence engine.

84. The method of claim 83, wherein the artificial intelligence engine is based on at least one of a neural network, a constraint program, fuzzy logic, classification, symbolic manipulation, fuzzy set theory, evolutionary computation, cybernetics, data mining, approximate reasoning, derivative-free optimization, and soft computing.

85. The method of claim 20, wherein processing comprises:

determining whether suitability of use information is maintained for the at least two selected beauty products;

when suitability of use information is maintained, processing information characterizing the at least two selected beauty products and the suitability of use information to thereby identify at least one additional product complementary to a combination of the at least two selected products; and when suitability of use information is not maintained, determining at least one additional product complementary to a combination of the at least two selected products using information characterizing the at least two selected beauty products and an artificial intelligence process.

86. The method of claim 20, wherein maintaining information about suitability of use comprises:

maintaining information about suitability of use of at least some of the plurality of beauty products with other of the plurality of beauty products, the information about suitability of use being derived from experts.

87. The method of claim 20, wherein maintaining information about suitability of use comprises:

maintaining information about suitability of use of at least some of the plurality of beauty products with other of the plurality of beauty products, the information about suitability of use being derived from artificial intelligence.

88. The method of claim 23, wherein accessing information about relationships comprises:

accessing through the artificial intelligence search engine information about relationships between at least some of the plurality of products, the information about relationships derived from experts.

89. The method of claim 23, wherein identifying at least one recommended product complementary to the at least one user-specified product comprises:

identifying, by the artificial intelligence engine, at least one recommended product that is complementary to the at least one user-specified product and that is compatible with the user in at least one of a physical, physiological, biological, and aesthetic aspect, using at least the information about product relationships.

* * * * *